US009897584B2

(12) United States Patent
Islam

(10) Patent No.: US 9,897,584 B2
(45) Date of Patent: *Feb. 20, 2018

(54) SHORT-WAVE INFRARED SUPER-CONTINUUM LASERS FOR NATURAL GAS LEAK DETECTION, EXPLORATION, AND OTHER ACTIVE REMOTE SENSING APPLICATIONS

(71) Applicant: OMNI MEDSCI, INC., Ann Arbor, MI (US)

(72) Inventor: Mohammed N. Islam, Ann Arbor, MI (US)

(73) Assignee: Omni Medsci, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/711,907

(22) Filed: Sep. 21, 2017

(65) Prior Publication Data

US 2018/0024104 A1    Jan. 25, 2018

Related U.S. Application Data

(60) Division of application No. 15/357,225, filed on Nov. 21, 2016, now Pat. No. 9,797,876, which is a
(Continued)

(51) Int. Cl.
*G01J 3/00* (2006.01)
*G01N 33/15* (2006.01)
(Continued)

(52) U.S. Cl.
CPC ........... *G01N 33/15* (2013.01); *A61B 5/0013* (2013.01); *A61B 5/0022* (2013.01);
(Continued)

(58) Field of Classification Search
CPC ...... G01J 3/02; G01J 3/28; G01J 3/42; G01N 21/31; G01N 21/552
(Continued)

(56) References Cited

U.S. PATENT DOCUMENTS 4,063,106 A    12/1977 Ashkin et al.
4,158,750 A     6/1979 Sakoe et al.
(Continued)

FOREIGN PATENT DOCUMENTS

CA         2 458 123         5/2012
DE    102010012987 A1    10/2010
(Continued)

OTHER PUBLICATIONS

Pan, Yingtian, et al., "Hand-held arthroscopic optical coherence tomography for in vivo high-resolution imaging of articular cartilage", Journal of Biomedical Optics 8(4), Oct. 2003, pp. 648-654.
(Continued)

*Primary Examiner* — Tarifur Chowdhury
*Assistant Examiner* — Md M Rahman
(74) *Attorney, Agent, or Firm* — Brooks Kushman P.C.

(57) ABSTRACT

A measurement system performs non-destructive quality control or constitutive analysis using a light source generating an output optical beam using semiconductor sources that generate an input optical beam, a multiplexer configured to receive the input beam and to form an intermediate optical beam, and fibers configured to receive the intermediate beam and to form the output beam. The fibers include a fused silica fiber having a core diameter less than 400 microns. The output beam includes wavelengths between 700 and 2500 nanometers and has a bandwidth of at least 10 nanometers. The system includes a measurement apparatus that receives the output beam and delivers the beam to a sample to generate a spectroscopy beam. A receiver is configured to
(Continued)

receive the spectroscopy beam and process the beam to generate an output signal. The light source and receiver are remote from the sample, which includes plastics or food industry goods.

17 Claims, 28 Drawing Sheets

Related U.S. Application Data continuation of application No. 14/650,981, filed as application No. PCT/US2013/075767 on Dec. 17, 2013, now Pat. No. 9,500,634.

(60) Provisional application No. 61/747,485, filed on Dec. 31, 2012.

(51) Int. Cl.
```
A61B 5/00        (2006.01)
G01N 33/49       (2006.01)
G01N 33/44       (2006.01)
G01N 33/02       (2006.01)
G01N 21/88       (2006.01)
G01N 21/3563     (2014.01)
G01N 21/359      (2014.01)
G01J 3/453       (2006.01)
A61B 5/145       (2006.01)
A61B 5/1455      (2006.01)
G01N 21/39       (2006.01)
G01M 3/38        (2006.01)
G01J 3/28        (2006.01)
G01J 3/10        (2006.01)
G01J 3/18        (2006.01)
G01J 3/14        (2006.01)
H01S 3/30        (2006.01)
```
(52) U.S. Cl.
CPC .......... *A61B 5/0075* (2013.01); *A61B 5/0086* (2013.01); *A61B 5/0088* (2013.01); *A61B 5/1455* (2013.01); *A61B 5/14532* (2013.01); *A61B 5/14546* (2013.01); *A61B 5/4547* (2013.01); *G01J 3/108* (2013.01); *G01J 3/28* (2013.01); *G01J 3/2823* (2013.01); *G01J 3/453* (2013.01); *G01N 21/359* (2013.01); *G01N 21/3563* (2013.01); *G01N 21/39* (2013.01); *G01N 21/88* (2013.01); *G01N 33/02* (2013.01); *G01N 33/442* (2013.01); *G01N 33/49* (2013.01); *A61B 2562/0233* (2013.01); *A61B 2562/0238* (2013.01); *A61B 2562/146* (2013.01); *A61B 2576/02* (2013.01); *G01J 3/14* (2013.01); *G01J 3/1838* (2013.01); *G01J 2003/104* (2013.01); *G01J 2003/2826* (2013.01); *G01M 3/38* (2013.01); *G01N 2021/399* (2013.01); *G01N 2201/061* (2013.01); *G01N 2201/062* (2013.01); *G01N 2201/08* (2013.01); *G01N 2201/12* (2013.01); *H01S 3/302* (2013.01)

(58) Field of Classification Search
USPC ....................................................... 356/300
See application file for complete search history.

(56) References Cited

U.S. PATENT DOCUMENTS

| | | |
|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,267,152 A | 11/1993 | Yang et al. |
| 5,267,256 A | 11/1993 | Saruwatari et al. |
| 5,267,323 A | 11/1993 | Kimura |
| 5,300,097 A | 4/1994 | Lerner et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,400,165 A | 3/1995 | Gnauck et al. |
| 5,408,409 A | 4/1995 | Glassman et al. |
| 5,458,122 A | 10/1995 | Hethuin |
| 5,544,654 A | 8/1996 | Murphy et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Mortara et al. |
| 5,718,234 A | 2/1998 | Warden et al. |
| 5,747,806 A | 5/1998 | Khalil |
| 5,748,103 A | 5/1998 | Flach et al. |
| 5,792,204 A | 8/1998 | Snell |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,043,927 A | 3/2000 | Islam |
| 6,115,673 A | 9/2000 | Malin |
| 6,185,535 B1 | 2/2001 | Hedin et al. |
| 6,200,309 B1 | 3/2001 | Rice et al. |
| 6,224,542 B1 | 5/2001 | Chang et al. |
| 6,246,707 B1 | 6/2001 | Yin et al. |
| 6,246,896 B1 | 6/2001 | Dumoulin |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne |
| 6,289,238 B1 | 9/2001 | Besson et al. |
| 6,301,271 B1 | 10/2001 | Sanders et al. |
| 6,301,273 B1 | 10/2001 | Sanders et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |

(56) References Cited

U.S. PATENT DOCUMENTS

| | | |
|---|---|---|
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,509,566 B1 | 1/2003 | Wamsley et al. |
| 6,512,936 B1 | 1/2003 | Monfre |
| 6,534,012 B1 | 3/2003 | Hazen et al. |
| 6,549,702 B2 | 4/2003 | Islam et al. |
| 6,567,431 B2 | 5/2003 | Tabirian et al. |
| 6,587,702 B1 | 7/2003 | Ruchti |
| 6,603,910 B2 | 8/2003 | Islam et al. |
| 6,605,080 B1 | 8/2003 | Altshuler et al. |
| 6,611,643 B2 | 8/2003 | Birk |
| 6,625,180 B2 | 9/2003 | Bufetov et al. |
| 6,631,025 B2 | 10/2003 | Islam et al. |
| 6,640,117 B2 | 10/2003 | Makarewicz |
| 6,659,947 B1 | 12/2003 | Carter et al. |
| 6,659,999 B1 | 12/2003 | Anderson et al. |
| 6,738,652 B2 | 5/2004 | Mattu |
| 6,760,148 B2 | 7/2004 | Islam |
| 6,773,922 B2 | 8/2004 | Jeng |
| 6,788,965 B2 | 9/2004 | Ruchti |
| 6,802,811 B1 | 10/2004 | Slepian |
| 6,816,241 B2 | 11/2004 | Grubisic |
| 6,847,336 B1 | 1/2005 | Lemelson |
| 6,864,978 B1 | 3/2005 | Hazen |
| 6,885,498 B2 | 4/2005 | Islam |
| 6,885,683 B1 | 4/2005 | Fermann et al. |
| 6,943,936 B2 | 9/2005 | Islam et al. |
| 6,990,364 B2 | 1/2006 | Ruchti |
| 7,010,336 B2 | 3/2006 | Lorenz |
| 7,027,467 B2 | 4/2006 | Baev et al. |
| 7,060,061 B2 | 6/2006 | Altshuler et al. |
| 7,133,710 B2 | 11/2006 | Acosta |
| 7,167,300 B2 | 1/2007 | Fermann et al. |
| 7,209,657 B1 | 4/2007 | Islam |
| 7,233,816 B2 | 6/2007 | Blank |
| 7,259,906 B1 | 8/2007 | Islam |
| 7,263,288 B1 | 8/2007 | Islam |
| 7,294,105 B1 | 11/2007 | Islam |
| 7,299,080 B2 | 11/2007 | Acosta |
| 7,317,938 B2 | 1/2008 | Lorenz |
| 7,318,909 B2 | 1/2008 | Lehmann et al. |
| 7,356,364 B1 | 4/2008 | Bullock et al. |
| 7,395,158 B2 | 7/2008 | Monfre |
| 7,433,116 B1 | 10/2008 | Islam |
| 7,519,253 B2 | 4/2009 | Islam |
| 7,519,406 B2 | 4/2009 | Blank |
| 7,620,674 B2 | 11/2009 | Ruchti |
| 7,697,966 B2 | 4/2010 | Monfre |
| 7,787,503 B2 | 8/2010 | Wadsworth |
| 7,787,924 B2 | 8/2010 | Acosta |
| 7,800,818 B2 | 9/2010 | Mattsson |
| 7,807,718 B2 | 10/2010 | Hashim |
| 8,000,574 B2 | 8/2011 | Buchter |
| 8,145,286 B2 | 3/2012 | Arai |
| 8,180,422 B2 | 5/2012 | Rebec |
| 8,198,589 B2 | 6/2012 | Tolton et al. |
| 8,472,108 B2 | 6/2013 | Islam |
| 9,207,121 B2 | 12/2015 | Adler |
| 2002/0013518 A1 | 1/2002 | West et al. |
| 2002/0019584 A1 | 2/2002 | Schulze et al. |
| 2002/0032468 A1 | 3/2002 | Hill et al. |
| 2002/0082612 A1 | 6/2002 | Moll et al. |
| 2002/0109621 A1 | 8/2002 | Khair et al. |
| 2002/0115914 A1 | 8/2002 | Russ |
| 2002/0128846 A1 | 9/2002 | Miller |
| 2002/0178003 A1 | 11/2002 | Gehrke et al. |
| 2003/0022126 A1 | 1/2003 | Buchalla |
| 2003/0107739 A1 | 6/2003 | Lehmann et al. |
| 2003/0109055 A1 | 6/2003 | Lehmann et al. |
| 2003/0152307 A1 | 8/2003 | Drasek et al. |
| 2004/0174914 A1 | 9/2004 | Fukatsu |
| 2004/0240037 A1 | 12/2004 | Harter |
| 2005/0111500 A1 | 5/2005 | Harter et al. |
| 2006/0223032 A1 | 10/2006 | Fried |
| 2006/0245461 A1 | 11/2006 | Islam |
| 2006/0268393 A1 | 11/2006 | Islam |
| 2007/0021670 A1 | 1/2007 | Mandelis et al. |
| 2007/0078348 A1 | 4/2007 | Holman |
| 2008/0105665 A1 | 5/2008 | Kondo |
| 2009/0028193 A1 | 1/2009 | Islam |
| 2009/0204110 A1 | 8/2009 | Islam |
| 2010/0046067 A1 | 2/2010 | Fermann et al. |
| 2010/0322490 A1 | 12/2010 | Pan |
| 2010/0331637 A1 | 12/2010 | Ting |
| 2011/0143364 A1 | 6/2011 | Kim |
| 2011/0282167 A1 | 11/2011 | Ridder et al. |
| 2012/0013722 A1 | 1/2012 | Wong |
| 2012/0239013 A1 | 9/2012 | Islam |
| 2013/0274569 A1 | 10/2013 | Islam |

FOREIGN PATENT DOCUMENTS

| | | |
|---|---|---|
| EP | 1148666 | 10/2001 |
| WO | 09715240 | 5/1997 |
| WO | 97049340 | 12/1997 |
| WO | 01150959 | 7/2001 |
| WO | 200189362 | 11/2001 |
| WO | 200227640 | 4/2002 |
| WO | 200228123 | 4/2002 |
| WO | 2005013843 A2 | 2/2005 |
| WO | 2007061772 A2 | 5/2007 |
| WO | 2009130464 A1 | 10/2009 |
| WO | 2013012938 | 1/2013 |

OTHER PUBLICATIONS

Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.

Dubois, A., et al., "Three-dimensional cellular-level imaging using full-field optical coherence tomography", Physics in Medicine and Biology, Phys. Med. Biol. 49, 2004, pp. 1227-1234.

Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.

Unterhuber, A., et al., "Advances in broad bandwidth light sources for ultrahigh resolution optical coherence tomography", Physics in Medicine and Biology, Phys. Med. Biol. 49, 2004, pp. 1235-1246.

Drexler, Wolfgang, "Ultrahigh-resolution optical coherence tomography", Journal of Biomedical Optics, vol. 9, No. 1, Jan./Feb. 2004, pp. 47-74.

Schmitt, Joseph, et al., "Intravascular Optical Coherence Tomography Opens a Window Onto Coronary Artery Disease", Optics & Photonics News, Feb. 2004, pp. 20-25.

Nassif, N.A., et al., "In vivo high-resolution video-rate spectral-domain optical coherence tomography of the human retina and optic nerve", Optics Express, vol. 12, No. 3, Feb. 9, 2004, pp. 367-376.

Choi, Seung-Ho, et al., "Observation of Optical Precursors in Water", Physical Review Letters, vol. 92, No. 19, May 14, 2004, pp. 193903-1-193903-.3.

Pierce, Mark C., et al., "Advances in Optical Coherence Tomography imaging for Dermatology", Optical Coherence Tomography Advances, The Journal of Investigative Dermatology, Sep. 3, 2004, pp. 458-461.

"State-Specific Trends in Chronic Kidney Failure—United States, 1990-2001", Morbidity and Mortality Weekly Report, Department of Health and Human Services Centers for Disease Control and

(56) References Cited

OTHER PUBLICATIONS

Prevention, vol. 53, No. 39, copied from internet: file:// C:\Documents and Settings\eturlo\Desktop\State-Specific Trends in Chronic Kidney . . . Feb. 12, 2010, Oct. 8, 2004, pp. 918-920.
I.B. Ads, A.A.E. Wagie, N.B. Mariun, A.B.E. Jammal, "An Internet-based blood pressure monitoring system for patients," Journal of Telemedicine and Telecare, 2001, pp. 51-53.
R.H. Istepanian, B. Woodward, P.A. Bales, S. Chen, B. Luk, "The comparative performance of mobile telemediCal systems based on the IS-54 and GSM cellular telephone standards," Journal of Telemedicine and Telecare, 1999, pp. 97-104.
Shaw, et al, IR Supercontinuum Generation in As—Se Photonic Crystal Fiber, Optical Society of America, Copyright 2005, 3 pages.
PCT/US06/44451, Notification of Transmittal of the International Search Report and the Written Opinion of the International Searching Authority, or the Declaration, dated Nov. 29, 2007, 12 pages.
G.S. Edwards et al., "Free-electron-laser-based biophysical and biomedical instrumentation," American Institute of Physics, vol. 74, No. 7, Jul. 2003, pp. 3207-3245.
Computer Motion, Inc., "501(k) Summary—ZEUS® MicroWrist™ Surgical System and Accessories," Sep. 24, 2002, 6 pages.
Computer Motion, Inc. "HERMES™ O.R. Control Center—510(k) Summary of Safety and Effectiveness," Oct. 11, 2002, 5 pages.
K.M. Joos, et al. "Optic Nerve Sheath Fenestration with a Novel Wavelength Produced by the Free Electron Laser (FEL)," Lasers in Surgery and Medicine, 27: 2000,191-205.
J. Sanghera, I. Aggarwal, "IR Fiber Optics at NRL," undated, 10 pages.
J. Sanghera, L.B. Shaw, I.D. Aggarwal, "Applications of chalcogenide glass optical fibers," Academic of Science, 2003, pp. 1-11.
B. Rigas, P.T.T. Wong, "Human Colon Adenocarcinoma Cell Lines Display Infrared Spectroscopic Features," Cancer Research, Jan. 1, 1992, pp. 84-88.
G. Edwards, et al., "Comparison of OPA and Mark-III FEL for Tissue Ablation at 6.45 Microns," Department of Physics and Free Electron Laser Laboratory, Duke University, 2002, 7 pages.
Glenn Edwards, "Biomedical and potential clinical applications for pulsed lasers operating near 6.45 um," Society of Photo-Optical Instrumentation Engineers, 1995, 2 pages.
Passat, "Solid-State Lasers and Optical Components," Jul. 14, 2003, 5 pages.
P.A. Thielen and L.B. Shaw, et al., "Small-core As—Se fiber for Raman amplification," Optics Leti-Ers, vol. 28, No. 16, Aug. 15, 2003, 3 pages.
R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.
U.S. Appl. No. 10/652,276, "System and Method for Voice Control of Medical levices," by Mohammed N. Islam, abandoned filed Aug. 29, 2003.
U.S. Appl. No. 10/757,341, "System and Method for Voice Control of Medical Devices," by Mohammed N. Islam, issued filed Jan. 13, 2004.
U.S. Appl. No. 12/206,432, "System and Method for Voice Control of Medical Devices," by Mohammed N. Islam, pending filed Sep. 8, 2008.
U.S. Patent and Trademark Office, Office Action for U.S. Appl. No. 12/206,432, filed Sep. 8, 2008, Mohammed N, Islam, dated Mar. 12, 2009.
U.S. Patent and Trademark Office, Notice of Allowance and Fee(s) Due for U.S. Appl. No. 12/206,432, filed Sep. 8, 2008, Mohammed N. Islam, dated Aug. 28, 2009.
Istepanian, Robert H., "The Comparative Performance of Mobile Telemedical Systems based on the IS-54 and GSM Cellular Telephone Standards"; Journal of Telemedicine and Telecare 1999; pp. 97-104.

Aris, Ishak Bin, "An Internet-Based Blood Pressure Monitoring System for Patients"; Journal of Telemedicine and Telecare 2001; pp. 51-53.
Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).
Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).
Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).
Borlinghaus, R.T., L. Kuschel, "White Light Laser: The Ultimate Source for Confocal Microscopy," http://www.leica-microsystems.com/science-lab/white-light-laser (Jun. 27, 2012).
Ziegler, U., A.G. Bittermann, M. Hoechli, "Introduction to Confocal Laser Scanning Microscopy (LEICA)," www.zmb.unizh.ch, May 29, 2013.
Islam, M. N., et al., "Broad bandwidths from frequency-shifting solitons in fibers", Optics Letters, vol. 14, No. 7, Apr. 1, 1989, pp. 370-372.
Islam, M. N., et al., "Femtosecond distributed soliton spectrum in fibers", J. Opt. Soc. Am. B, vol. 6, No. 6, Jun. 1989, pp. 1149-1158.
Busse, Lynda E., et al., "Design Parameters for Fluoride Multimode Fibers", Journal of Lightwave Technology, vol. 9, No. 7, Jul. 1991, pp. 828-831.
Wuthrich, Stefan, et al., "Optical damage thresholds at 2.94 um in fluoride glass fibers", Applied Optics, vol. 31, No. 27, Sep. 20, 1992, pp. 5833-5837.
Inoue, H., et al., "Computer simulation of the vibrational spectra and properties of fluoride glasses based on ZrF4", Journal of Non-Crystalline Solids, vol. 161, 1993, pp. 118-122.
Mizunami, Toru, et al., "Gain saturation characteristics of Raman amplification in silica and fluoride glass optical fibers", Optics Communications 97, 1993, pp. 74-78.
Desthieux, B., et al., "111 kW (0. 5 mJ) pulse amplification at 1.5 um using a gated cascade of three erbium-doped fiber amplifiers," Appl. Phys. Lett. vol. 63, Aug. 2, 1993, pp. 586-588.
Edwards, Glenn, et al., Tissue ablation by a free-electron laser tuned to the amide II band, Nature, vol. 371, Sep. 29, 1994, pp. 416-419.
Borrelli, N. F., et al., "Resonant and non-resonant effects in photonic glasses", Journal of Non-Crystalline Solids 185, 1995, pp. 109-122.
Asobe, Masaki, et al., "Third-order nonlinear spectroscopy in As2S3 chalcogenide glass fibers", J. Appl. Phys. 77 (11), Jun. 1, 1995, pp. 5518-5523.
Jarman, Richard H., "Novel optical fiber lasers", Current Opinion in Solid State and Materials Science, 1996, pp. 199-203.
Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.
Asobe, Masaki, "Nonlinear Optical Properties of Chalcogenide Glass Fibers and Their Application to All-Optical Switching", Optical Fiber Technology, vol. 3, Article No. OF970214, 1997, pp. 142-148.
Smektala, F., et al., "Chalcogenide glasses with large non-linear refractive indices", Journal of Non-Crystalline Solids 239, 1998, pp. 139-142.
Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pages 216-235.
Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.
Nowak, G. A., et al., "Low-power high-efficiency wavelength conversion based on modulational instability in high-nonlinearity fiber," Optics Letters, vol. 23, No. 12, Jun. 15, 1998, pp. 936-938.

(56) References Cited

OTHER PUBLICATIONS

Cardinal, T., et al., "Non-linear optical properties of chalcogenide glasses in the system As—S—Se", Journal of Non-Crystalline Solids 256 & 257, 1999, pp. 353-360.

Lucas, Jacques, "Infrared glasses", Current Opinion in Solid State & Materials Science 4, 1999. pp. 181-187.

Sanghera, J. S., et al., Active and passive chalcogenide glass optical fibers for IR applications: a review, Journal of Non-Crystalline Solids 256 & 257, 1999, pp. 6-16.

Nishida, Yoshiki, et al., "Reliability of Fluoride Fiber Module for Optical Amplifier Use", IEEE Photonics Technology Letters, vol. 11, No. 12, Dec. 1999, pp. 1596-1598.

Nowak, George A., et al., "Stable supercontinuum generation in short lengths of conventional dispersion-shifted fiber", Applied Optics, vol. 38, No. 36, Dec. 20, 1999, pp. 7364-7369.

Urban, J. P. G., et al., "The Nucleus of the Intervertebral Disc from Development to Degeneration" Amer. Zool., vol. 40, 2000, pp. 53-61.

Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.

Ranka, Jinendra K., et al., "Visible continuum generation in air-silica microstructure optical fibers with anomalous dispersion at 800 nm", Optics Letters, vol. 25, No. 1, Jan. 1, 2000, pp. 25-27.

Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.

Boult, Maggi, et aL, "Percutaneous Endoscopic Laser Discectomy", Systematic Review, Aust. N.Z.J. Surg., vol. 70, Apr. 7, 2000, pp. 475-479.

Camacho, Nancy P., et al., "FTIR Microscopic Imaging of Collagen and Proteoglycan in Bovine Cartilage," Biopolymers (Biospectroscopy), vol. 62, 2001, pp. 1-8.

Choi, Joon Y., et al, "Thermal, Mechanical, Optical, and Morphologic Changes in Bovine Nucleus Pulposus Induced by Nd:YAG ($\lambda$=1.32 um) Laser Irradiation", Lasers in Surgery and Medicine, vol. 28, 2001, pp. 248-254.

Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, 2001, pp. 33-37.

Jackson, Stuart D., et al., "Theory and numerical simulation of nth-order cascaded Raman fiber lasers", J. Opt. Soc. Am. B, vol. 18, No. 9, Sep. 2001, pp. 1297-1306.

Werle, Peter, et al., "Near- and mid-infrared laser-optical sensors for gas analysis", Optics and Lasers in Engineering 37, 2002, pp. 101-114.

Beck, Mattias, et al., "Continuous Wave Operation of a Mid-Infrared Semiconductor Laser at Room Temperature," Science vol. 295, www.sciencemag.org, Jan. 11, 2002, pp. 301-305.

Harbold, J. M., et al., "Highly nonlinear As—S—Se glasses for all-optical switching", Optics Letters, vol. 27, No. 2, Jan. 15, 2002, pp. 119-121.

Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.

Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.

Harbold, Jeffrey M., et al., "Highly Nonlinear Ge—As—Se and. Ge—As—S—Se Glasses for All-Optical Switching", IEEE Photonics Technology Letters, vol. 14, No. 6, Jun. 2002, pp. 822-824.

Husakou, Anton V., et al, "Supercontinuum generation, four-wave mixing, and fission of higher-order solitons in photonic-crystal fibers", J. Opt. Soc. Am. B, vol. 19, No. 9, Sep. 2002, pp. 2171-2182.

Wadsworth, William J., et al., "Supercontinuum generation in photonic crystal fibers and Dptical fiber tapers: a novel light source", J. Opt. Soc. Am. B, vol. 19, No. 9, Sep. 2002, pp. 2148-2155.

Kumar, V.V. Ravi Kanth, et al, "Extruded soft glass photonic crystal fiber for ultrabroad supercontinuum generation", Optics Express, vol. 10, No. 25, Dec. 16, 2002, pp. 1520-1525.

Edwards, Glenn S., et al., "Advantage of the Mark-III FEL for biophysical research and biomedical applications", J. Synchrotron Rad. vol. 10, 2003, pp. 354-357.

Nicholson, J. W., et al., "Pulsed and continuous-wave supercontinuum generation in highly nonlinear, dispersion-shifted fibers", Applied Physics B 77, 2003, pp. 211-218.

Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.

Nicholson, J. W., et al., "All-fiber, octave-spanning supercontinuum", Optics Letters, vol. 28, No. 8, Apr. 15, 2003, pp. 643-645.

Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.

"New and Emerging Techniques—Surgical, Rapid Review, Laser Discectomy", Australian Safety and Efficacy Register of New Interventional Procedures—Surgical, Jun. 2003, 12 pages.

Avdokhin, A. V., et al, "Continuous-wave, high-power, Raman continuum generation in holey fibers", Optics Letters, vol. 28, No. 15, Aug. 1, 2003, pp. 1353-1355.

Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.

Slusher, Richard, et al., "Highly nonlinear composite chalcogenide/polymer fibers", OSA 2004, 1 page.

Thongtrangan, Issada, et al., "Minimally invasive spinal surgery: a historical perspective", Neurosurg. Focus, vol. 16, Article 13, Jan. 2004, pp. 1-10.

Vinay V. Alexander et al.; Modulation Instability High Power All-Fiber Supercontinuum Lasers and Their Applications; Optical Fiber Technology 18; 2012; pp. 349-374.

Robert S. Jones et al.; Near-Infrared Transillumination at 1310-nm for the Imaging of Early Dental Decay; vol. 11, No. 18; Optics Express 2259; Sep. 8, 2003.

Extended European Search Report for European Application No. 13861874.3 dated Jul. 15, 2016.

Extended European Search Report for European Application No. 13861892.5 dated Jul. 22, 2016.

Lee, Ju Han, et al., "Continuous-wave supercontinuum laser based on an erbium-doped fiber ring cavity incorporating a highly nonlinear optical fiber", Optics Letters, vol. 30, No. 19, Oct. 1, 2005, pp. 2599-2601.

Genty, G., et al., "Supercontinuum generation in large mode-area microstructured fibers", Optics Express, vol. 13, No. 21, Oct. 17, 2005, pp. 8625-8633.

Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.

Travers, J. C., et al., "Extended blue supercontinuum generation in cascaded holey fibers", Optics Letters, vol. 30, No. 23, Dec. 1, 2005, pp. 3132-3134.

Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.

Moon, Sucbei, et al., "Generation of octave-spanning supercontinuum with I550-nm amplified diode-laser pulses and a dispersion-shifted fiber", Optics Express, vol. 14, No. 1, Jan. 9, 2006, pp. 270-278.

Fedotova, O., et al., "Supercontinuum generation in planar rib waveguides enabled by anomalous dispersion", Optics Express, vol. 14, No. 4, Feb. 20, 2006, pp. 1512-1517.

(56) References Cited

OTHER PUBLICATIONS

Harrington, James A., "Infrared Fiber Optics", OSA Handbook, vol. III, white paper, to be published by McGraw Hill, Undated, 13 pages.
Aaviksoo, J., et al., "Observation of optical precursors at pulse propagation in GaAs", Physical Review A, vol. 44, No. 9, Nov. 1, 1991, pp. R5353-R5356.
Boppart, Stephen A., et al., "Imaging developing neural morphology using optical coherence tomography", Journal of Neuroscience Methods 70, 1996, pp. 65-72.
Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.
Tearney, Guillermo J., et al., "In vivo Endoscopic Optical Biopsy with Optical Coherence Tomography", Science, New Series, vol. 276, Jun. 27, 1997, pp. 2037-2039.
de Boer, Johannes F., et al., "Imaging thermally damaged tissue by polarization sensitive Optical coherence tomography", Optics Express 212, vol. 3, No. 6, Sep. 14,1998, pp. 212-218.
Roggan, Andre, et al., "Optical Properties of Circulating Human Blood in the Wavelength Range 400-2500 NM", Journal of Biomedical Optics, vol. 4, No. 1, Jan. 1999, pp. 36-46.
de Boer, Johannes F., et al., "Determination of the depth-resolved Stokes parameters of light backscattered from turbid media by use of polarization-sensitive optical coherence tomography", Optics Letters, vol. 24, No. 5; Mar. 1, 1999, pp. 300-302.
Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.
D'Amico, Anthony V., et al., "Optical Coherence Tomography as a Method for Identifying Benign and Malignant Microscopic Structures in the Prostate Gland", Basic Science, Urology 55 (5), 2000, pp. 783-787.
Li, Xingde, et al., "Imaging needle for optical coherence tomography", Optics Letters, vol. 25, No. 20, Oct. 15, 2000, pp. 1520-1522.
Oughstun, Kurt E., "Influence of precursor fields on ultrashort pulse autocorrelation measurements and pulse width evolution", Optics Express, vol. 8, No. 8, Apr. 9, 2001, pp. 481-491.
Kowalevicz, Andrew M., et al., "Ultrahigh resolution optical coherence tomography using a superluminescent light source" Optics Express 349, vol. 10, No. 7, Apr. 8, 2002, pp. 349-353.
Povazay, B., et al., "Submicrometer axial resolution optical coherence tomography", Optics Letters, vol. 27, No. 20, Oct. 15, 2002, pp. 1800-1802.
Xie, T.-Q., et al., "Detection of tumorigenesis in urinary bladder with optical coherence tomography: optical characterization of morphological changes", Optics Express, vol. 10, No. 24, Dec. 2, 2002, 2003, pp. 1431-1441.
Seefeldt, Michael, et al., "Compact white-light source with an average output power of 2.4 Wand 900 nm spectral bandwidth", Optics Communications 216, pp. 199-202.
Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.
Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.
Hori, Takashi, et al., "Flatly broadened, wideband and low noise supercontinuum generation in highly nonlinear hybrid fiber", Optics Express, vol. 12, No. 2, Jan. 26, 2004, pp. 317-324.
Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.
Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.

Venugopalan, V., "Optical Society of America Biomed Topical Meeting Tutorial on Tissue Optics", Apr. 27, 2004, pp. 1-32.
Slusher, Richart E., et al., "Large Raman gain and nonlinear phase shifts in high-purity As2So3 chalcogenide fibers", J. Opt. Soc. Am. B, vol. 21, No. 6, Jun. 2004, pp. 1146-1155.
Leon-Saval, S. G., et al., "Supercontinuum generation in submicron fibre waveguides", Optics Express, vol. 12, No. 13, Jun. 28, 2004, pp. 2864-2869.
Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.
Genty, G., et al., "Enhanced bandwidth of supercontinuum generated m microstructured fibers", Optics Express, vol. 12, No. 15, Jul. 26, 2004, pp. 3471-3480.
Champert, Pierre-Alain, et al., "White-light supercontinuum generation in normally dispersive optical fiber using original multi-wavelength pumping system", Optics Express, vol. 12, No. 19, Sep. 20, 2004, pp. 4366-4371.
Nicholson, J. W., "Supercontinuum generation in ultraviolet-irradiated fibers", Optics Letters, vol. 29, No. 20, Oct. 15, 2004, pp. 2363-2365.
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.
Demircan, Ayhan, et al., "Supercontinuum generation by the modulation instability", Optics Communications 244, 2005, pp. 181-185.
Papemyi, S. B., et al., "Sixth-Order Cascaded Raman Amplification", OFC/NFOEC, 2005, 3 pages.
Tanaka, Keiji, "Optical nonlinearity in photonic glasses", Journal of Materials Science: Materials in Electronics 16, 2005, pp. 633-643.
Westbrook, Paul S., "Improved Supercontinuum Generation Through UV Processing of Highly Nonlinear Fibers", Journal of Lightwave Technology, vol. 23, No. 1, Jan. 2005, pp. 13-18.
Abeeluck, Akheelesh K., et al., "Continuous-wave pumping in the anomalous- and normal dispersion regimes of nonlinear fibers for supercontinuum generation", Optics Letters, vol. 30, No. 1, Jan. 1, 2005, pp. 61-63.
Kutz, J. Nathan, et al., Enhanced Supercontinuum Generation through Dispersion-Management, Optics Express, vol. 13, No. 11, May 30, 2005, pp. 3989-3998.
Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.
Saliminia, A., et al., "Ultra-broad and coherent white light generation in silica glass by focused femtosecond pulses at 1.5pm", Optics Express, vol. 13, No. 15, Jul. 25, 2005, pp. 5731-5738.
Takushima, Yuichi, High average power, depolarized super-continuum generation using a 1.55-um ASE noise source, Optics Express, vol. 13, No. 15, Jul. 25, 2005, pp. 5871.-5877.
Travers, J. C., et al., "Extended continuous-wave supercontinuum generation in a low-water-loss holey fiber", Optics Letters, vol. 30, No. 15, Aug. 1, 2005, pp. 1938-1940.
Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.
Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.
Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).

(56) References Cited

OTHER PUBLICATIONS

Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Troy, T.L., S.N. Thennadil, "Optical properties of human skin in the near infrared wavelength range of 1000 to 2200nm," Journal of Biomedical Optics, vol. 6, No. 2, pp. 167-176, (2001).
Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).
Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).
Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).
Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Harman-Boehm, I. A. Gal, A.M. Raykhman, J.D. Zahn, E Naidis, Y. Mayzel, "Noninvasive glucose monitoring: a novel approach," Journal of Diabetes Science and Technology, vol. 3, No. 2 pp. 253-260 (2009).
Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).
Smith, J.L., "The Pursuit of Noninvasive Glucose: Hunting the Deceitful Turkey," 2nd Edition, pp. 1-141 (2011).
Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).
Lussi, A., R. Hibst, R. Paulus, "Diagnodent: An optical method for caries detection," Journal of Dental Research, vol. 83, special issue C, pp. C80-C83 (2004).
Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).
Zakian, C., I. Pretty, R. Ellwood, "Near-infrared hyperspectral imaging of teeth for dental caries detection," Journal of Biomedical Optics, vol. 16, No. 6, 064047 (2009).
Belikov, A.V., A.V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).
Karlsson, L. "Caries detection methods based on changes in optical properties between healthy and carious issue," International Journal of Dentistry, vol. 2010, Article ID 270729, 9 pages (2010).

Fried, D. M. Staninec, C.L. Darling, "Near-infrared imaging of dental decay at 1310nm," Journal of Laser Dentistry, vol. 18, No. 1, pp. 8-16 (2010).
Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).
Maia, A., L. Karlsson, W. Margulis, A. Gomes, "Evaluation of two imaging techniques: near-infrared transillumination and dental radiographs for the detection of early approximal enamel caries," Dentomaxillofacial Radiology, vol. 40, pp. 429-433 (2011).
Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).
Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
Nishizawa, N., "Generation and application of high-quality supercontinuum sources," Optical Fiber Technology, vol. 18, pp. 394-402 (2012).
Watari, M., H. Migashiyama, N. Mitsui, M. Tomo, Y. Ozaki, "On-line monitoring of the density of linear low-density polyethylene in a real plant by near-infrared spectroscopy and chemometrics," Applied Spectroscopy, vol. 58, No. 2, pp. 248-255 (2004).
Tolton, B.T., "A concept for a gas-filter correlation radiometer to remotely sense the atmospheric carbon dioxide column from space," Notes and Correspondence, Journal of Atmospheric and Oceanic Technology, vol. 21, pp. 837-852, (May 2004).
Nunnally, W.C., S.K. Holland, G. Laufer, "Wide field of view solar occultation gas filter correlation radiometer for stratospheric methane measurements from a sounding rocket," Thermosense XXV, K.E. Elliot, X.P. Maldague, Editors, Proceedings of SPIE, vol. 5073, pp. 122-130 (2003).
Xiao, J. Q. Tian, Y. Lu, L. Wang, X. Qi, B. Wen, "Extraction of hydrocarbon content information by using hyperspectral image at Liaodong Bay, China," downloaded from world wide web on Apr. 6, 2012.
McCoy, R.M., J.G. Blake, K.L. Andrews, "Detecting hydrocarbon microseepage," Oil and Gas Journal, pp. 40-45 (May 28, 2001).
Van Der Meer, F. P. Van Dijk, H. Van Der Werff, H. Yang, "Remote sensing and petroleum seepage: a review and case study," Terra Nova, vol. 14, No. 1, pp. 1-17 (2002).
Van Der Meer, F., P. Van Dijk, S. Kroonenberg, Y. Hong, H. Lang, "Hyperspectral hydrocarbon microseepage detection and monitoring: potentials and limitations," Second EARSEI workshop on imaging spectroscopy, pp. 1-9 (2000).
Andreoli, G. B. Bulgarelli, B. Hosgood, D. Tarchi, "Hyperspectral analysis of oil and oil-impacted soils for remote sensing purposes," Institute for the Protection and Security of the Citizen, European Commission Joint Research Centre, EUR 22739 EN (Mar. 2007).
S.D. Khan, S. Jacobson, "Remote sensing and geochemistry for detecting hydrocarbon microseepages," GSA Bulletin, vol. 120, No. 1/2, pp. 96-105 (Jan./Feb. 2008).
F. Kuhn, K. Oppermann, B. Horig, "Hydrocarbon Index—and algorithm for hyperspectral detection of hydrocarbons," International Journal of Remote Sensing, vol. 25, No. 12, pp. 2467-2473 (Jun. 20, 2004).
Shu-Fang, T. C. Jian-Ping, Z. Mi, "The information of oil and gas micro-seepage in Dongsheng Region of Inner Mongolia extraction based on the airborne hyperspectral remote sensing image," Remote Sensing of the Environment, 16th National Symposium on Remote Sensing of China, edited by Q. Tong, Proceedings of SPIE, vol. 7123, 71230K-1 to 8, (2008).

(56) References Cited

OTHER PUBLICATIONS

Xu, D., G. Ni, T. Jiang, L. Jiang, M. Chi, "Integration of field work and hyperspectral data for oil and gas exploration," IEEE 1-4244-1212-9/07, pp. 3194-3197 (2007).

Ku, D-Q, G-Q Ni, L-L Jiang, Y-T Shen, T. Li, S-L Ge, X-B Shu, "Exploring for natural gas using reflectance spectra of surface soils," Advances in Space Research, vol. 41, pp. 1800-1817 (2008).

M. Kumar, M.N. Islam, F.L. Terry, M.J. Freeman, A. Chan, M. Neelakandan, T. Manzur, "Stand-off Detection of solid targets with diffuse reflection spectroscopy using a high-power mid-infrared supercontinuum source," Applied Optics, vol. 51, No. 15, pp. 2794-2807 (May 20, 2012).

Clark, R.N., J.M. Curchin, T. M. Hoefen, G.A. Swayze, "Reflectance Spectroscopy of organic compounds: 1. Alkanes," Journal of Geophysical Research, vol. 114, pp. EO3001 1 to 19, (2009).

International Search Report and Written Opinion for International Application No. PCT/US2013/075767 dated Oct. 14, 2014.

International Preliminary Report on Patentability for International Application No. PCT/US2013/07567 dated Jul. 9, 2015.

SHORT-WAVE INFRARED SUPER-CONTINUUM LASERS FOR NATURAL GAS LEAK DETECTION, EXPLORATION, AND OTHER ACTIVE REMOTE SENSING APPLICATIONS

CROSS-REFERENCE TO RELATED APPLICATIONS

This application is a divisional of U.S. application Ser. No. 15/357,225 filed Nov. 21, 2016, which is a continuation of U.S. application Ser. No. 14/650,981 filed Jun. 10, 2015, now U.S. Pat. No. 9,500,634, issued Nov. 22, 2016, which is the U.S. national phase of PCT Application No. PCT/US2013/075767 filed Dec. 17, 2013, which claims the benefit of U.S. provisional application Ser. No. 61/747,485 filed Dec. 31, 2012, the disclosure of which is hereby incorporated by reference in its entirety.

This application is related to U.S. provisional application Ser. No. 61/747,472 filed Dec. 31, 2012; U.S. provisional application Ser. No. 61/747,477 filed Dec. 31, 2012; Ser. No. 61/747,481 filed Dec. 31, 2012; Ser. No. 61/747,487 filed Dec. 31, 2012; Ser. No. 61/747,492 filed Dec. 31, 2012; Ser. No. 61/747,553 filed Dec. 31, 2012; and Ser. No. 61/754,698 filed Jan. 21, 2013, the disclosures of which are hereby incorporated in their entirety by reference herein.

This application has a common priority date with commonly owned U.S. application Ser. No. 14/650,899 filed Jun. 10, 2015, which is the U.S. national phase of International Application PCT/US2013/075700 entitled Near-Infrared Lasers For Non-Invasive Monitoring Of Glucose, Ketones, HBA1C, And Other Blood Constituents; International Application PCT/US2013/075736 entitled Short-Wave Infrared Super-Continuum Lasers For Early Detection Of Dental Caries; U.S. application Ser. No. 14/108,995 filed Dec. 17, 2013 entitled Focused Near-Infrared Lasers For Non-Invasive Vasectomy And Other Thermal Coagulation Or Occlusion Procedures; U.S. application Ser. No. 14/108,986 filed Dec. 17, 2013, now U.S. Pat. No. 9,164,032 entitled Short-Wave Infrared Super-Continuum Lasers For Detecting Counterfeit Or Illicit Drugs And Pharmaceutical Process Control; U.S. application Ser. No. 14/108,974 filed Dec. 17, 2013 entitled Non-Invasive Treatment Of Varicose Veins; and U.S. application Ser. No. 14/109,007 filed Dec. 17, 2013 entitled Near-Infrared Super-Continuum Lasers For Early Detection Of Breast And Other Cancers, the disclosures of which are hereby incorporated in their entirety by reference herein.

BACKGROUND AND SUMMARY

Remote sensing or hyper-spectral imaging often uses the sun for illumination, and the short-wave infrared (SWIR) windows of about 1.5-1.8 microns and about 2-2.5 microns may be attractive because the atmosphere transmits in these wavelength ranges. Although the sun can be a bright and stable light source, its illumination may be affected by the time-of-day variations in the sun angle as well as weather conditions. For example, the sun may be advantageously used for applications such as hyper-spectral imaging only between about 9 am to 3 pm, and it may be difficult to use the sun during cloudy days or during inclement weather. In one embodiment, the hyper-spectral sensors measure the reflected solar signal at hundreds (e.g., 100 to 200+) contiguous and narrow wavelength bands (e.g., bandwidth between 5 nm and 10 nm). Hyper-spectral images may provide spectral information to identify and distinguish between spectrally similar materials, providing the ability to make proper distinctions among materials with only subtle signature differences. In the SWIR wavelength range, numerous gases, liquids and solids have unique chemical signatures, particularly materials comprising hydro-carbon bonds, O—H bonds, N—H bonds, etc. Therefore, spectroscopy in the SWIR may be attractive for stand-off or remote sensing of materials based on their chemical signature, which may complement other imaging information.

A SWIR super-continuum (SC) source may be able to replace at least in part the sun as an illumination source for active remote sensing, spectroscopy, or hyper-spectral imaging. In one embodiment, reflected light spectroscopy may be implemented using the SWIR light source, where the spectral reflectance can be the ratio of reflected energy to incident energy as a function of wavelength. Reflectance varies with wavelength for most materials because energy at certain wavelengths may be scattered or absorbed to different degrees. Using a SWIR light source may permit 24/7 detection of solids, liquids, or gases based on their chemical signatures. As an example, natural gas leak detection and exploration may require the detection of methane and ethane, whose primary constituents include hydro-carbons. In the SWIR, for instance, methane and ethane exhibit various overtone and combination bands for vibrational and rotational resonances of hydro-carbons. In one embodiment, diffuse reflection spectroscopy or absorption spectroscopy may be used to detect the presence of natural gas. The detection system may include a gas filter correlation radiometer, in a particular embodiment. Also, one embodiment of the SWIR light source may be an all-fiber integrated SWIR SC source, which leverages the mature technologies from the telecommunications and fiber optics industry. Beyond natural gas, active remote sensing in the SWIR may also be used to identify other materials such as vegetation, greenhouse gases or environmental pollutants, soils and rocks, plastics, illicit drugs, counterfeit drugs, firearms and explosives, paints, and various building materials.

In one embodiment, a measurement system comprises a light source configured to generate an output optical beam. The light source comprises a plurality of semiconductor sources configured to generate an input optical beam, a multiplexer configured to receive at least a portion of the input optical beam and to form an intermediate optical beam, and one or more fibers configured to receive at least a portion of the intermediate optical beam and to form the output optical beam. At least a portion of the one or more fibers comprises a fused silica fiber having a core diameter less than 400 microns. The output optical beam comprises one or more optical wavelengths, at least a portion of which are between 700 nanometers and 2500 nanometers, and has a bandwidth of at least 10 nanometers. The measurement system also includes a measurement apparatus configured to receive a received portion of the output optical beam and to deliver a delivered portion of the output optical beam to a sample, wherein the delivered portion of the output optical beam is configured to generate a spectroscopy output beam from the sample. A receiver is configured to receive at least a portion of the spectroscopy output beam having a bandwidth of at least 10 nanometers and to process the at least a portion of the spectroscopy output beam to generate an output signal. The light source and the receiver are remote from the sample, which comprises plastics or food industry goods, and the measurement system performs non-destructive quality control or constitutive analysis.

In one embodiment, a measurement system comprises a light source configured to generate an output optical beam.

The light source comprises a plurality of semiconductor sources configured to generate an input optical beam, a multiplexer configured to receive at least a portion of the input optical beam and to form an intermediate optical beam, and one or more fibers configured to receive at least a portion of the intermediate optical beam and to form the output optical beam. At least a portion of the one or more fibers comprises a fused silica fiber having a core diameter less than 400 microns and the output optical beam comprises one or more optical wavelengths, at least a portion of which are between 700 nanometers and 2500 nanometers, with a bandwidth of at least 10 nanometers. The system includes a measurement apparatus configured to receive a received portion of the output optical beam and to deliver a delivered portion of the output optical beam to a sample, wherein the delivered portion of the output optical beam is configured to generate a spectroscopy output beam from the sample. A receiver is configured to receive at least a portion of the spectroscopy output beam having a bandwidth of at least 10 nanometers and to process the at least a portion of the spectroscopy output beam to generate an output signal. The light source and the receiver are remote from the sample, which comprises plastics or food industry goods.

In one embodiment, a method of measuring comprises generating an output optical beam, comprising generating an input optical beam from a plurality of semiconductor sources, multiplexing at least a portion of the input optical beam and forming an intermediate optical beam, and guiding at least a portion of the intermediate optical beam using one or more fibers including a fused silica fiber having a core diameter less than 400 microns. The method includes broadening a spectrum of at least a portion of the intermediate optical beam to at least 10 nanometers to form the output optical beam with an output beam broadened spectrum, wherein the output optical beam comprises one or more optical wavelengths between 700 nanometers and 2500 nanometers. The method also includes receiving a received portion of the output optical beam and delivering a delivered portion of the output optical beam to a sample comprising plastics or food industry goods located remotely from the generated output optical beam, and generating a spectroscopy output beam having a bandwidth of at least 10 nanometers from the sample, wherein the spectroscopy output beam comprises spectral features based on a chemical composition of the sample. The method further includes receiving at least a portion of the spectroscopy output beam, and processing the at least a portion of the spectroscopy output beam and generating an output signal.

In one embodiment, a measurement system comprises a light source configured to generate an output optical beam, the light source comprising one or more semiconductor sources configured to generate an input beam, one or more optical amplifiers configured to receive at least a portion of the input beam and to deliver an intermediate beam to an output end of the one or more optical amplifiers, one or more optical fibers configured to receive at least a portion of the intermediate beam and to deliver at least the portion of the intermediate beam to a distal end of the one or more optical fibers to form a first optical beam, a nonlinear element configured to receive at least a portion of the first optical beam and to broaden a spectrum associated with the at least a portion of the first optical beam to at least 10 nm through a nonlinear effect in the nonlinear element to form the output optical beam with an output beam broadened spectrum, wherein at least a portion of the output beam broadened spectrum comprises a near-infrared wavelength between approximately 700 nanometers and approximately 2500 nanometers, and wherein at least a portion of the one or more fibers is a fused silica fiber with a core diameter less than approximately 400 microns. The system also includes a measurement apparatus configured to receive a received portion of the output optical beam and to deliver a delivered portion of the output optical beam to a sample, wherein the delivered portion of the output optical beam is configured to generate a spectroscopy output beam from the sample, and a receiver configured to receive at least a portion of the spectroscopy output beam having a bandwidth of at least 10 nanometers and to process the at least a portion of the spectroscopy output beam to generate an output signal, wherein the light source and the receiver are remote from the sample, and wherein the sample comprises plastics or food industry goods.

In another embodiment, a measurement system comprises a light source configured to generate an output optical beam, the light source comprising a plurality of semiconductor sources configured to generate an input optical beam, a multiplexer configured to receive at least a portion of the input optical beam and to form an intermediate optical beam, one or more fibers configured to receive at least a portion of the intermediate optical beam and to form the output optical beam, wherein at least a portion of the one or more fibers comprises a fused silica fiber having a core diameter less than approximately 400 microns, wherein the output optical beam comprises one or more optical wavelengths, at least a portion of which are between approximately 700 nanometers and approximately 2500 nanometers, and wherein the output optical beam has a bandwidth of at least 10 nanometers. The system includes a measurement apparatus configured to receive a received portion of the output optical beam and to deliver a delivered portion of the output optical beam to a sample, wherein the delivered portion of the output optical beam is configured to generate a spectroscopy output beam from the sample, and a receiver configured to receive at least a portion of the spectroscopy output beam having a bandwidth of at least 10 nanometers and to process the at least a portion of the spectroscopy output beam to generate an output signal, wherein the light source and the receiver are remote from the sample, and wherein the sample comprises plastics or food industry goods.

In another embodiment, a method of measuring comprises generating an output optical beam comprising generating an input optical beam from a plurality of semiconductor sources, multiplexing at least a portion of the input optical beam and forming an intermediate optical beam, guiding at least a portion of the intermediate optical beam using one or more fibers including a fused silica fiber having a core diameter less than 400 microns, and broadening a spectrum of at least a portion of the intermediate optical beam to at least 10 nanometers to form the output optical beam with an output beam broadened spectrum, wherein the output optical beam comprises one or more optical wavelengths between 700 nanometers and 2500 nanometers. The method also includes receiving a received portion of the output optical beam and delivering a delivered portion of the output optical beam to a sample comprising plastics or food industry goods located remotely from the generated output optical beam, generating a spectroscopy output beam having a bandwidth of at least 10 nanometers from the sample, wherein the spectroscopy output beam comprises spectral features of hydrocarbons or organic compounds, receiving at least a portion of the spectroscopy output beam, and processing the at least a portion of the spectroscopy output beam and generating an output signal.

BRIEF DESCRIPTION OF THE DRAWINGS

For a more complete understanding of the present disclosure, and for further features and advantages thereof, reference is now made to the following description taken in conjunction with the accompanying drawings, in which.

DETAILED DESCRIPTION OF EXAMPLE EMBODIMENTS

As required, detailed embodiments of the present disclosure are described herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

One advantage of optical systems is that they can perform non-contact, stand-off or remote sensing distance spectroscopy of various materials. For remote sensing particularly, it may also be necessary to operate in atmospheric transmission windows. For example, two windows in the SWIR that transmit through the atmosphere are approximately 1.4-1.8 microns and 2-2.5 microns. In general, the near-infrared region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 1:
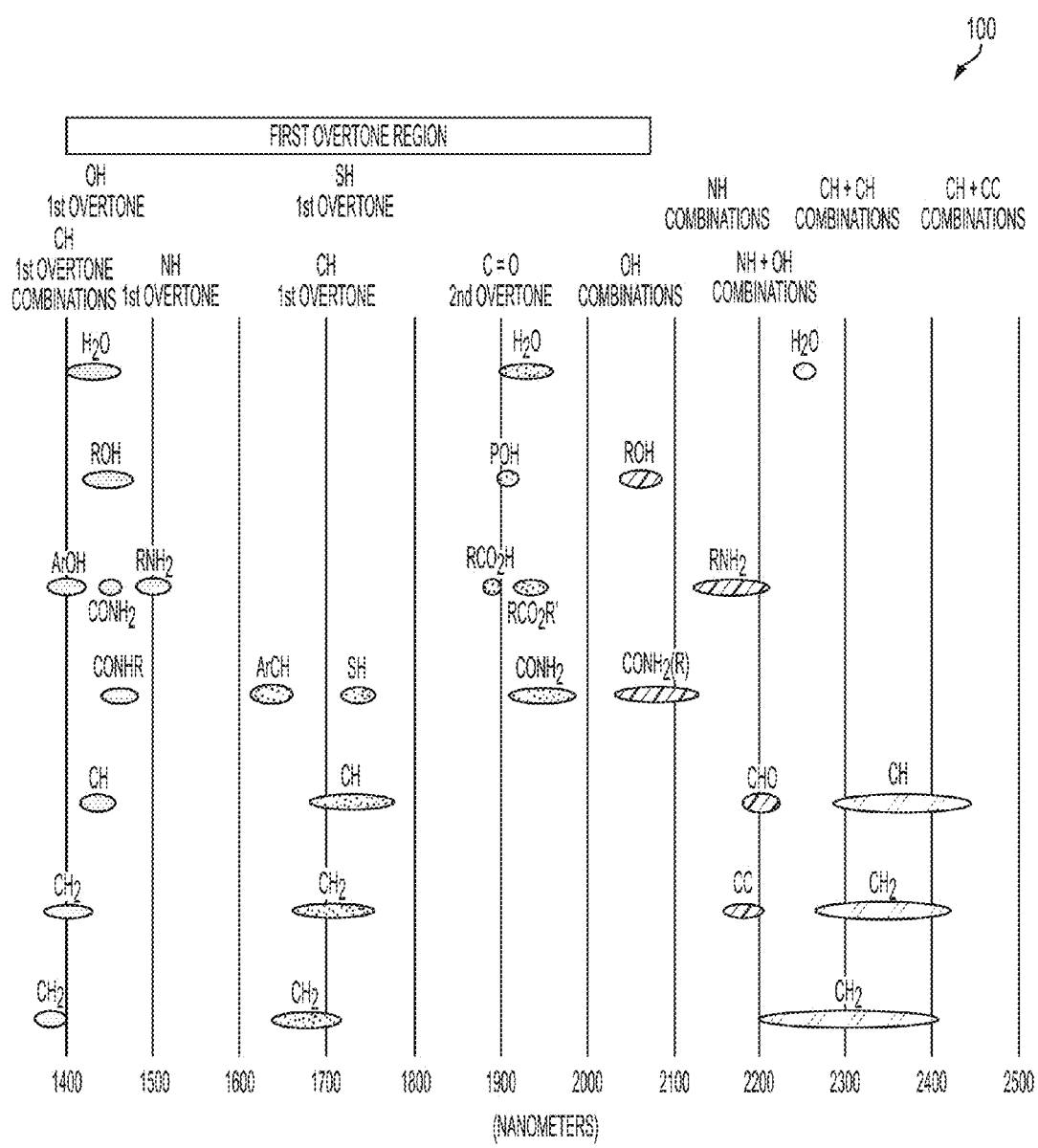
FIG. 1 illustrates wavelength bands for different chemical compounds over the SWIR wavelength range of approximately 1400 nm to 2500 nm. Also indicated are whether the bands are overtone or combination bands.

The SWIR wavelength range may be particularly valuable for identifying materials based on their chemical composition because the wavelength range comprises overtones and combination bands for numerous chemical bonds. As an example, FIG. 1 illustrates some of the wavelength bands for different chemical compositions. In 100 is plotted wavelength ranges in the SWIR (between 1400 and 2500 nm) for different chemical compounds that have vibrational or rotational resonances, along with whether the bands are overtone or combination bands. Numerous hydro-carbons are represented, along with oxygen-hydrogen and carbon-oxygen bonds. Thus, gases, liquids and solids that comprise these chemical compounds may exhibit spectral features in the SWIR wavelength range. In a particular embodiment, the spectra of organic compounds may be dominated by the C—H stretch. The C—H stretch fundamental occurs near 3.4 microns, the first overtone is near 1.7 microns, and a combination band occurs near 2.3 microns.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging the sun may be used as the illumination source, and the daytime illumination may comprise direct solar illumination as well as scattered solar (skylight), which is caused by the presence of the atmosphere. However, the sun illumination changes with time of day, clouds or inclement weather may block the sun light, and the sun light is not accessible in the night time. Therefore, it would be advantageous to have a broadband light source covering the SWIR that may be used in place of the sun to identify or classify materials in remote sensing or stand-off detection applications.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, parametric amplification, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this disclosure, the term "remote sensing" may include the measuring of properties of an object from a distance, without physically sampling the object, for example by detection of the interactions of the object with an electromagnetic field. In one embodiment, the electromagnetic field may be in the optical wavelength range, including the infrared or SWIR. One particular form of remote sensing may be stand-off detection, which may range from non-contact up to hundreds of meters away, for example.

Remote Sensing of Natural Gas Leaks

Natural gas may be a hydro-carbon gas mixture comprising primarily methane, with other hydro-carbons, carbon dioxide, nitrogen and hydrogen sulfide. Natural gas is important because it is an important energy source to provide heating and electricity. Moreover, it may also be used as fuel for vehicles and as a chemical feedstock in the manufacture of plastics and other commercially important organic chemicals. Although methane is the primary component of natural gas, to uniquely identify natural gas through spectroscopy requires monitoring of both methane and ethane. If only methane is used, then areas like cow pastures could be mistaken for natural gas fields or leaks. More specifically, the typical composition of natural gas is as follows:

| Component | Range (mole %) |
|---|---|
| Methane | 87.0-96.0 |
| Ethane | 1.5-5.1 |
| Propane | 0.1-1.5 |
| Iso-butane | 0.01-0.3 |
| Normal-butane | 0.01-0.3 |
| Iso-pentane | Trace-0.14 |
| Normal-pentane | Trace-0.04 |
| Hexanes plus | Trace-0.06 |
| Nitrogen | 0.7-5.6 |
| Carbon dioxide | 0.1-1.0 |
| Oxygen | 0.01-0.1 |
| Hydrogen | Trace-0.02 |

As one example of remote sensing of natural gas, a helicopter or aircraft may be flown at some elevation. The light source for remote sensing may direct the light beam toward the ground, and the diffuse reflected light may then be measured using a detection system on the aircraft. Thus, the helicopter or aircraft may be sampling a column area below it for natural gas, or whatever the material of interest is. In yet another embodiment, the column may sense aerosols of various sorts, as an example. Various kinds of SWIR light sources will be discussed later in this disclosure. The detection system may comprise, in one embodiment, a spectrometer followed by one or more detectors. In another embodiment, the detection system may be a dispersive element (examples include prisms, gratings, or other wavelength separators) followed by one or more detectors or detector arrays. In yet another embodiment, the detection system may comprise a gas-filter correlation radiometer. These are merely specific examples of the detection system, but combinations of these or other detection systems may also be used and are contemplated within the scope of this disclosure. Also, the use of aircraft is one particular example of a remote sensing system, but other system configurations may also be used and are included in the scope of this disclosure. For example, the light source and detection system may be placed in a fixed location, and for reflection the light source and detectors may be close to one another, while for transmission the light source and detectors may be at different locations. In yet another embodiment, the system could be placed on a vehicle such as an automobile or a truck, or the light source could be placed on one vehicle, while the detection system is on another vehicle. If the light source and detection system are compact and lightweight, they might even be carried by a person in the field, either in their hands or in a backpack.

Both methane and ethane are hydro-carbons with unique spectral signatures. For example, ethane is $C_2H_6$, while methane is $CH_4$. Also, methane and ethane have infrared absorption bands near 1.6 microns, 2.4 microns, 3.3 microns and 7 microns. It should be noted that the approximately 7 micron lines cannot be observed generally due to atmospheric absorption. Although the fundamental lines near 3.3 microns are stronger absorption features, the light sources and detectors in the mid-infrared may be more difficult to implement. Hence, the focus here is on observing the SWIR lines that fall in atmospheric transparency windows.

Figure 2A:
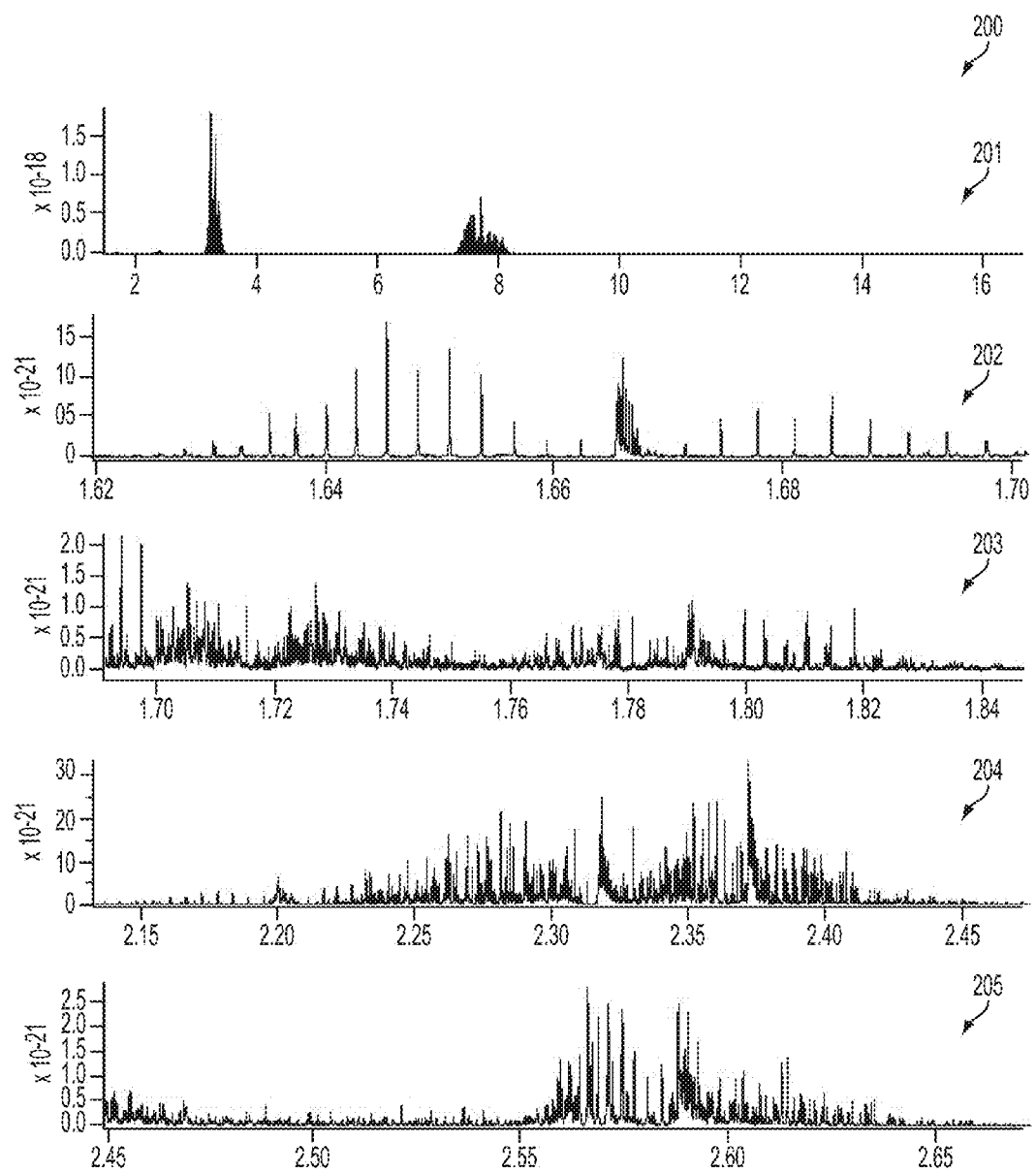
FIGS. 2A-2B show the absorption spectra for methane and ethane, respectively.
Figure 2B:
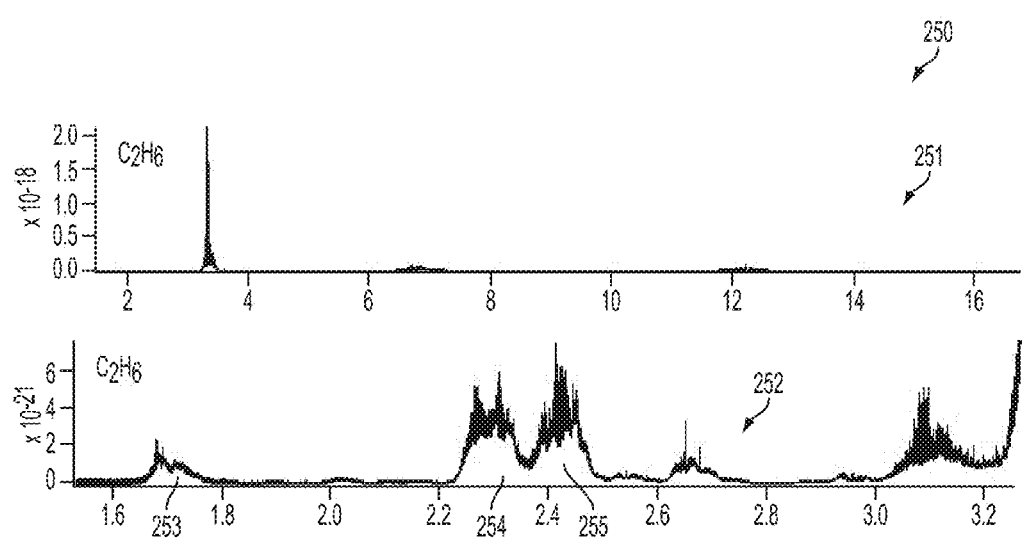

FIG. 2 illustrates the absorption spectra for methane (FIG. 2A) and ethane (FIG. 2B) (from http://vpl.astro.washington.edu/spectra). The curves 200 plot on a linear scale the absorption cross-section versus wavelength (in microns) for various methane lines. The curve 201 covers the wavelength range between approximately 1.5-16 microns, while the curves below provide blown-up views of different wavelength ranges (202 for approximately 1.62-1.7 microns, 203 for approximately 1.7-1.84 microns, 204 for approximately 2.15-2.45 microns, and 205 for approximately 2.45-2.65 microns). The curves 202 and 203 fall within about the first SWIR atmospheric transmission window between approximately 1.4-1.8 microns, while the curves 204 and 205 fall within the second SWIR atmospheric transmission window between approximately 2-2.5 microns. As can be seen, there are numerous spectral features for identifying methane in the SWIR. In addition, there are even stronger features near 3.4-3.6 microns and around 7-8 microns, although these require different light sources and detection systems.

FIG. 2B illustrates the absorption spectra for ethane. The curves 250 plot on a linear scale the absorption cross-section versus wavelength (in microns) for various ethane lines. The curve 251 covers the wavelength range between approximately 1.5-16 microns, while the curve 252 expands the scale between about 1.6-3.2 microns. The features 253 fall within about the first SWIR atmospheric transmission window between approximately 1.4-1.8 microns, while the features 254 and 255 fall within the second SWIR atmospheric transmission window between approximately 2-2.5 microns. There are distinct spectral features for identifying ethane as well in the SWIR. In addition, there are even stronger features near 3.4-3.6 microns and around 7 microns.

For detecting natural gas leaks, a SWIR light source and a detection system could be used in transmission or reflection. The area surrounding the source or natural gas pipeline may be surveyed, and the detection system may monitor the methane and ethane concentration, or even the presence of these two gases. The region may be scanned to cover an area larger than the laser beam. Also, if a certain quantity of natural gas is detected, an alarm may be set-off to alert the operator or people nearby. This is just one example of the natural gas leak detection, but other configurations and techniques may be used and are intended to be covered by this disclosure.

Natural gas leak detection is one example where active remote sensing or hyper-spectral imaging can be used to detect hydro-carbons or organic compounds. However, there are many other examples where the technique may be used to perform reflectance spectroscopy of organic compounds, and these are also intended to be covered by this disclosure. In one particular embodiment, alkanes may be detected, where alkanes are hydro-carbon molecules comprising single carbon-carbon bonds. Alkanes have the general formula $C_nH_{2n+2}$ and are open chain, aliphatic or non-cyclic molecules. Below are examples of some of the alkanes, which include methane and ethane, as well as more complicated compounds.

| | Formula |
|---|---|
| Methane | $CH_4$ |
| Ethane | $C_2H_6$ |
| Propane | $C_3H_8$ |
| Butane | $C_4H_{10}$ |

-continued

| | Formula |
|---|---|
| Pentane | $C_5H_{12}$ |
| Hexane | $C_6H_{14}$ |
| Heptane | $C_7H_{16}$ |
| Octane | $C_8H_{18}$ |
| Nonane | $C_9H_{20}$ |
| Decane | $C_{10}H_{22}$ |
| Paraffin | $C_{20+}C_{42+}$ |
| Polyethylene (LDPE, HDPE) | $(C_2H_4)_n$ or $(CH_2CH_2)_n$ |
| Polyvinylchloride (PVC) | $(C_2H_3Cl)_n$ or $(CHClCH_2)_n$ |
| Polypropylene | $(C_3H_5)_n$ or $\{CH(CH_3)CH_2\}_n$ |
| Polyethylene terephthalate (PETE) | $C_{10}H_8O_4$ or $\{(CO_2)_2C_6H_4(CH_2)_2\}_n$ |
| Nylon (polyamide) | $C_{12}H_{24}O_4N_2$ or $\{C_{10}H_{22}(CO_2)_2(NH)_2\}_n$ |

Figure 3:
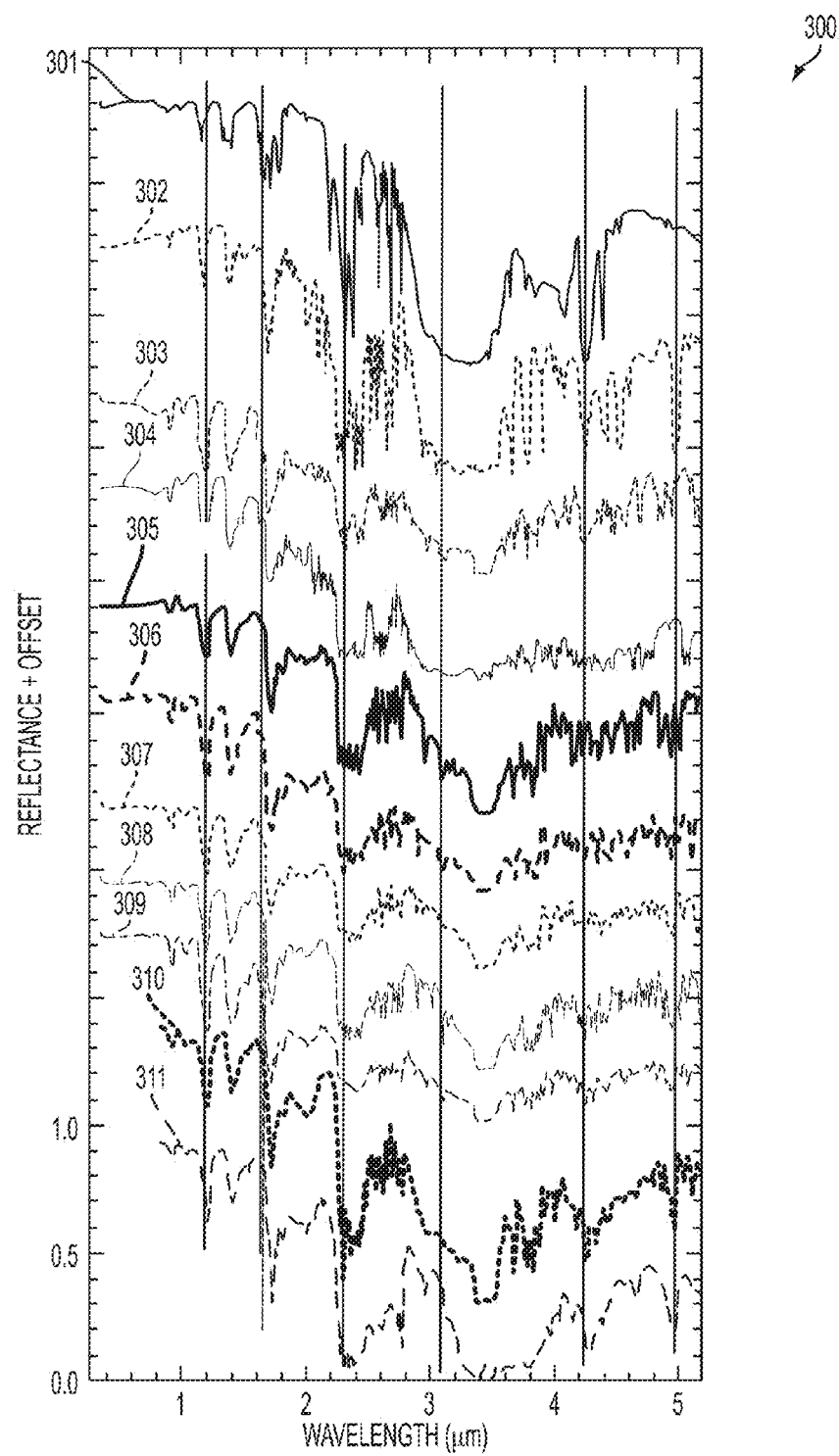
FIG. 3 illustrates the reflectance spectra for some members of the alkane family plus paraffin.

FIG. 3 illustrates the reflectance spectra 300 for some members of the alkane family plus paraffin. The vertical lines indicate positions of constant wavelength and are aligned with apparent absorptions in the methane spectrum at 1.19, 1.67, 2.32, 3.1, 4.23 and 4.99 microns. The spectra ore offset to enable easier viewing, and the offsets are of the following amounts: 301 methane 4.1; 302 ethane 3.6; 303 propane 3.3; 304 butane 2.8; 305 pentane 2.3; 306 hexane 2.0; 307 heptane 1.5; 308 octane 1.2; 309 nonane 0.85; 310 decane 0.4; and 311 paraffin 0.05. The reflectance of alkanes in the near-infrared may be dominated by absorptions due to combinations and overtones of bands at longer wavelengths. Although this wavelength range is mostly unexplored by organic spectroscopists, the near-infrared may be valuable for terrestrial and planetary remote sensing studies. Alkanes may have the fundamental absorptions due to a variety of C—H stretches between approximately 3.3-3.5 microns. The first overtone may be a relatively deep triplet near 1.7 microns. This triplet appears in most of the series, but the exact wavelength position may move. Another absorption band may be present near 1.2 microns, and this is likely the second overtone of the C—H stretch. The third C—H stretch overtone is near 0.9 microns. There is yet another near-infrared feature near 1.396 microns, which may correspond to the combinations of the first overtone of the C—H stretch with each of the two C—H band positions at approximately 1.35 microns and 1.37 microns. Moreover, there may be complex absorptions between 2.2-2.5 microns. For example, there may be a number of narrow individual absorption bands atop an overall absorption suite about 0.3 microns wide. A few absorption lines retain their location for most of the series 300, notably the 2.311 micron and 2.355 micron absorptions. This wavelength window may have multiple combinations and overtones, including contributions from the C—H stretch, $CH_3$ asymmetric bend combination, and C—H stretch/$CH_3$ symmetric bend combination.

Remote Sensing for Natural Gas Exploration

In addition to remote sensing to detect natural gas leaks, the same or similar system could also be used to explore for natural gas fields, whether under land or under water. Whereas a natural gas leak from a pipeline or building may be above the ground or only a few meters below the ground, natural gas exploration may occur for gas and oil that are much further below the ground, or under the water in a bay, lake, sea or ocean. For example, the exploration for natural gas and oil may be performed by determining the reflectance spectra of surface anomalies. The surface manifestations of oil and gas reservoirs may be used to map the petroleum potential of an area, particularly related to the seepage of oil and gas to the surface along faults or imperfect reservoir seals. The visible products of such seepage (e.g., oil and tar deposits) are generally referred to as macro-seeps, whereas the invisible gaseous products may be referred to as micro-seeps.

Figures 4A, 4B:
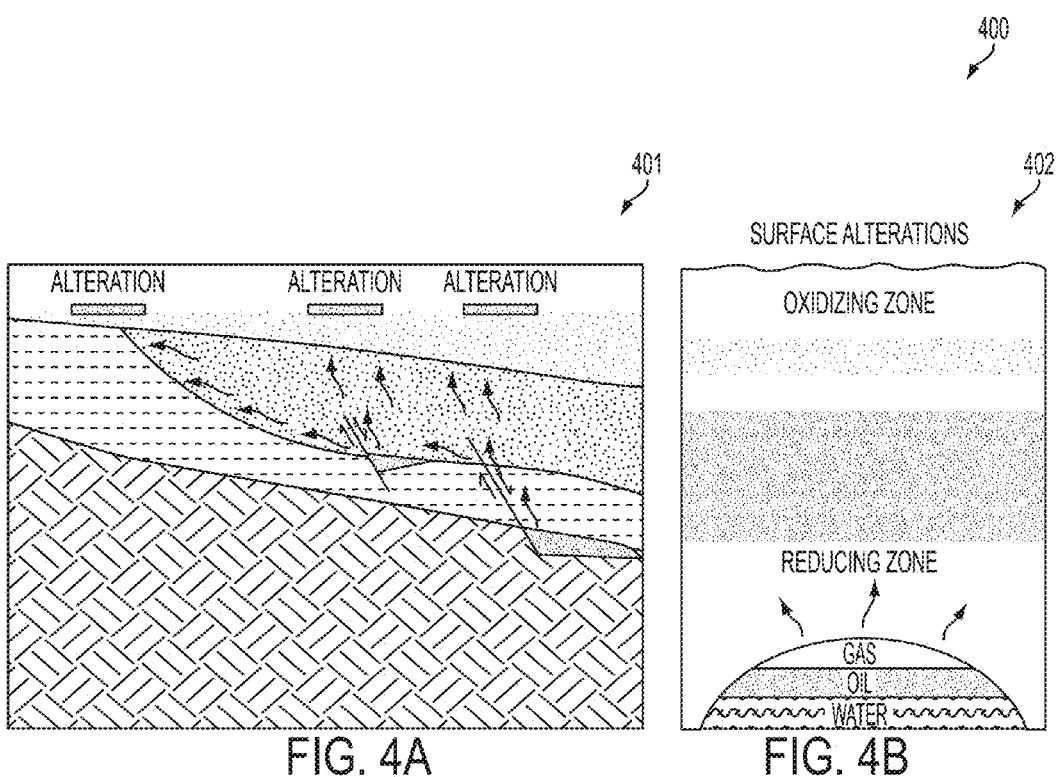
FIG. 4A depicts that micro-seepages may result from the vertical movement of hydro-carbons from their respective reservoirs to the surface. It is assumed that the rock column, including the seal rock, comprises interconnected fractures or micro-fracture systems.
FIG. 4B illustrates that surface alterations may occur because leaking hydro-carbons set up near-surface oxidation and/or reduction zones that favor the development of a diverse array of chemical and mineralogical changes.

As illustrated by 400 in FIG. 4, micro-seepages may result from the vertical movement of hydrocarbons 401 from their respective reservoirs to the surface. These hydrocarbon micro-seepages involve buoyant, relatively rapid, vertical ascent of ultra-small bubbles of light hydrocarbons (primarily methane through the butanes) through a network of interconnected, groundwater-filled joints and bedding planes (401). One of the assumptions required for micro-seepage to occur is that a rock column, including the seal rock, comprises extensive interconnected fractures or micro-fracture systems.

Direct detection methods may involve measurements of hydrocarbons, either in the form of oil accumulations or concentrations of escaping vapors, such as methane through butane. In addition, there are also indirect methods that may involve the measurement of secondary alternations that arise from the seepage of the hydrocarbons. For instance, hydrocarbon-induced alterations may include microbial anomalies, mineralogical changes, bleaching of red beds, clay mineral alterations, and electrochemical changes. These alterations occur because leaking hydrocarbons set up near-surface oxidation and/or reduction zones that favor the development of a diverse array of chemical and mineralogical changes, c.f. 402 in FIG. 4. Such alterations 402 may be distinct from adjacent rocks and, thus, may in some instance be detectable by various remote sensing techniques.

The diagnostic spectral features of methane and crude oil may comprise four distinct hydrocarbon absorption bands. For example, two bands near 1.18 microns and 1.38 microns may be narrow and sharply defined, although they may also be fairly weak. The other two spectral features may be near 1.68-1.72 microns and 2.3-2.45 microns; these bands may be broader, but they are also stronger than the previous two bands. The bands near 1.7 microns and 2.3 microns are spectral overtones or combinations of C—H vibrational modes. Moreover, hydrocarbon induced alterations associated with indirect detection may express themselves in a variety of spectral changes, such as mineralogical changes (calcium carbonate mineralization, near 2.35 microns), bleaching of red beds (near 1 micron), and clay minerals alterations (near 2.2 microns), among other changes.

Figure 5A:
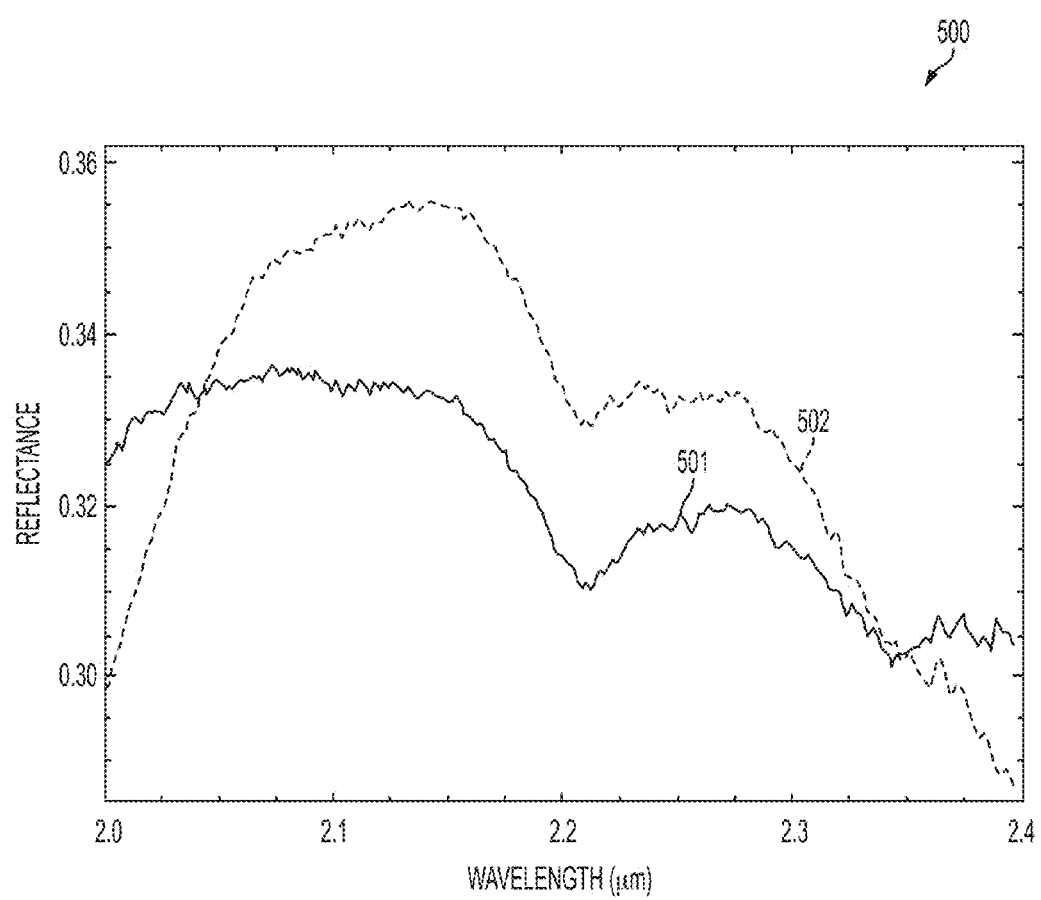
FIG. 5A shows the reflectance spectra for locations with natural gas fields (501) and locations without natural gas fields (502).

Various field tests have been conducted that verify the spectral signatures associated with natural gas fields, either land-based or water-based (e.g., in bays). In one example shown in FIG. 5A, the reflectance spectra 500 was collected for different locations between approximately 2 microns and 2.4 microns. In 501 the reflectance is plotted versus wavelength for locations with gas fields, while in 502 the reflectance is plotted for locations without gas fields. The macroscopic features of the reflectance spectra of surface soils show two broad absorption bands near 2.2 microns and 2.33 microns with complex shapes. The slightly positive slope in the region of 2.3-2.4 microns with natural gas suggests that hydrocarbons are overriding the spectral signature of clays in this region.

Figure 5B:
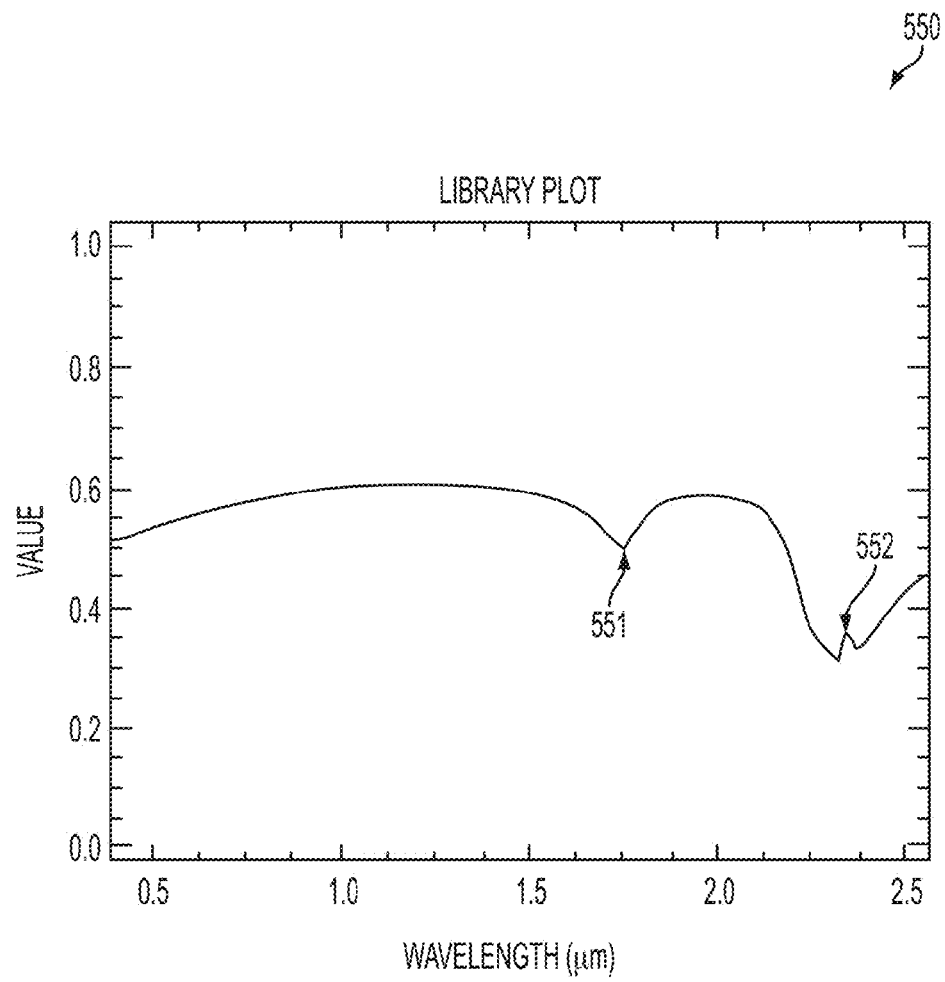
FIG. 5B illustrates spectra from field tests over regions with natural gas, which show two spectral features: one near 1.725 microns and another doublet between about 2.311 microns and 2.36 microns.

In yet another embodiment, field tests were conducted over a wider spectra range from approximately 0.5 microns to 2.5 microns (FIG. 5B). As the curve 550 illustrates, two absorption features are found for the hydrocarbon spectral reflectance curve: one near 1.725 microns 551 and a double absorption at approximately 2.311-2.36 microns 552. Thus, in these two field trial examples, oil-gas reservoir areas were identifiable using feature bands of 1650-1750 nm and 2000-2400 nm. In addition, the remote sensing method may be used for off-shore oil and gas exploration and marine pollution investigation, to name just a few examples.

Other Uses of Active Remote Sensing or Hyperspectral Imaging

Active and/or hyper-spectral remote sensing may be used in a wide array of applications. Although originally developed for mining and geology (the ability of spectral imaging to identify various minerals may be ideal for the mining and oil industries, where it can be used to look for ore and oil), hyper-spectral remote sensing has spread to fields as diverse as ecology and surveillance. The table below illustrates some of the applications that can benefit from hyper-spectral remote sensing.

| | |
|---|---|
| Atmosphere | water vapor, cloud properties, aerosols |
| Ecology | chlorophyll, leaf water, cellulose, pigments, lignin |
| Geology | mineral and soil types |
| Coastal Waters | chlorophyll, phytoplankton, dissolved organic materials, suspended sediments |
| Snow/Ice | snow cover fraction, grainsize, melting |
| Biomass Burning | subpixel temperatures, smoke |
| Commercial | mineral (oil) exploration, agriculture and forest production |

Figure 6:
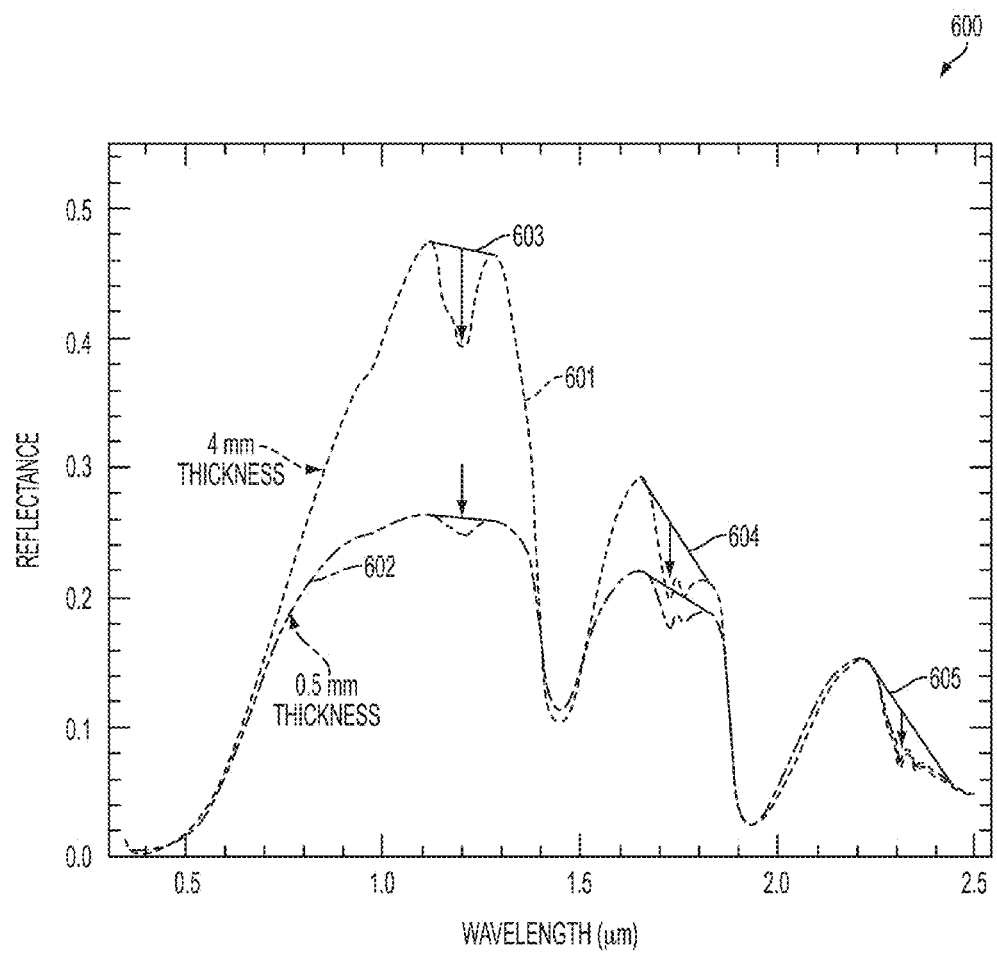
FIG. 6 shows the reflectance spectra of a sample of oil emulsion from the Gulf of Mexico 2010 oil spill (different thicknesses of oil).

In one embodiment, near-infrared imaging spectroscopy data may be used to create qualitative images of thick oil or oil spills on water. This may provide a rapid remote sensing method to map the locations of thick parts of an oil spill. While color imagery may show locations of thick oil, it is difficult to assess relative thickness or volume with just color imagery. As an example, FIG. 6 illustrates the reflectance spectra 600 of a sample of oil emulsion from the Gulf of Mexico 2010 oil spill. Curve 601 is a 4 mm thickness of oil, while curve 602 is a 0.5 mm thickness. Whereas the data in the visible hardly changes with oil thickness, in the near-infrared the change in reflectance spectra is much more dependent on the oil thickness. The data shows, for example, the C—H features near 1.2 microns 603, 1.73 microns 604, and 2.3 microns 605. Thus, in the infrared wavelengths, both the reflectance levels and absorption features due to organic compounds may vary in strength with oil thickness.

Figure 7:
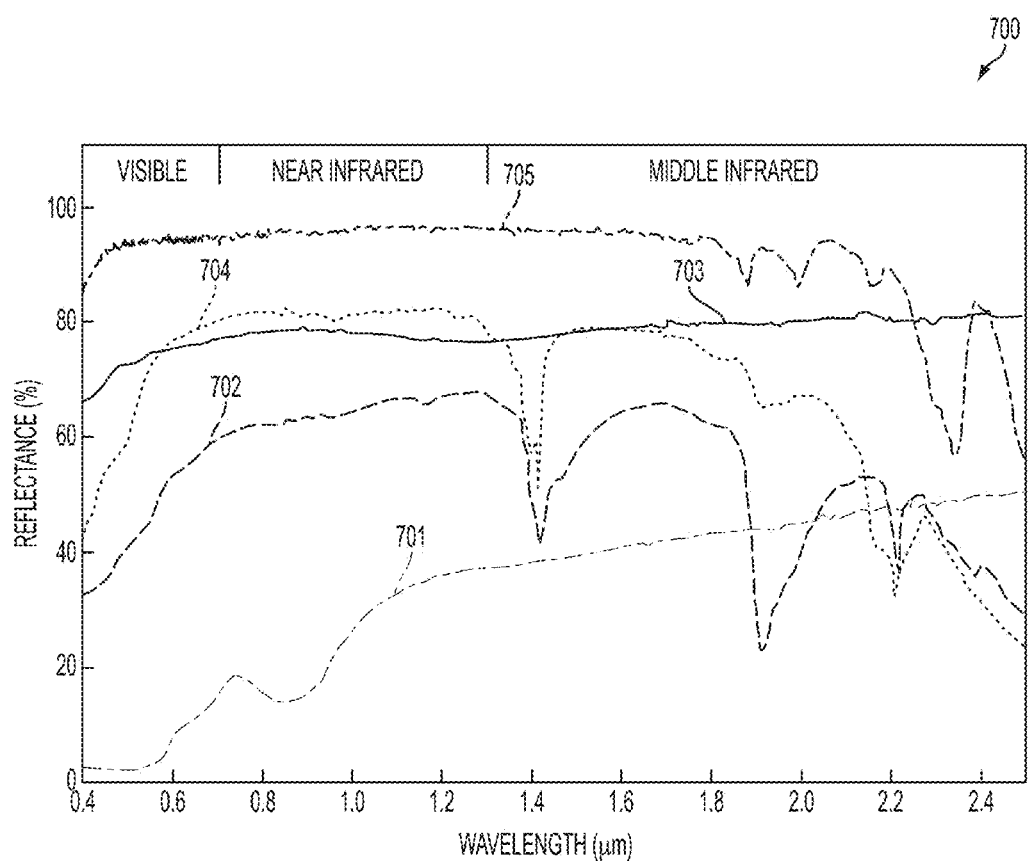
FIG. 7 illustrates the reflectance spectra of some representative minerals that may be major components of rocks and soils.

Remote sensing may also be used for geology and mineralogy mapping or inspection. FIG. 7 shows the reflectance spectra 700 for some representative minerals that are major components of rocks and soils. In inorganic materials such as minerals, chemical composition and crystalline structure may control the shape of the spectral curve and the locations of absorption bands. Wavelength-specific absorption may arise from particular chemical elements or ions and the geometry of chemical bonds between elements, which is related to the crystal structure. In hematite 701, the strong absorption in the visible may be caused by ferric iron. In calcite 705, the carbonate ion may be responsible for the series of absorption bands between 1.8 and 2.4 microns. Kaolinite 704 and montmorillonite 702 are clay minerals common in soils. The strong absorption near 1.4 microns in both spectra, along with a weak 1.9 micron band in kaolinite arise from the hydroxide ions, while the stronger 1.9 micron band in montmorillonite may be caused by bound water molecules in the hydrous clay. In contrast to these spectra, orthoclase feldspar 703, a dominant mineral in granite, shows very little absorption features in the visible or infrared.

Figure 8:
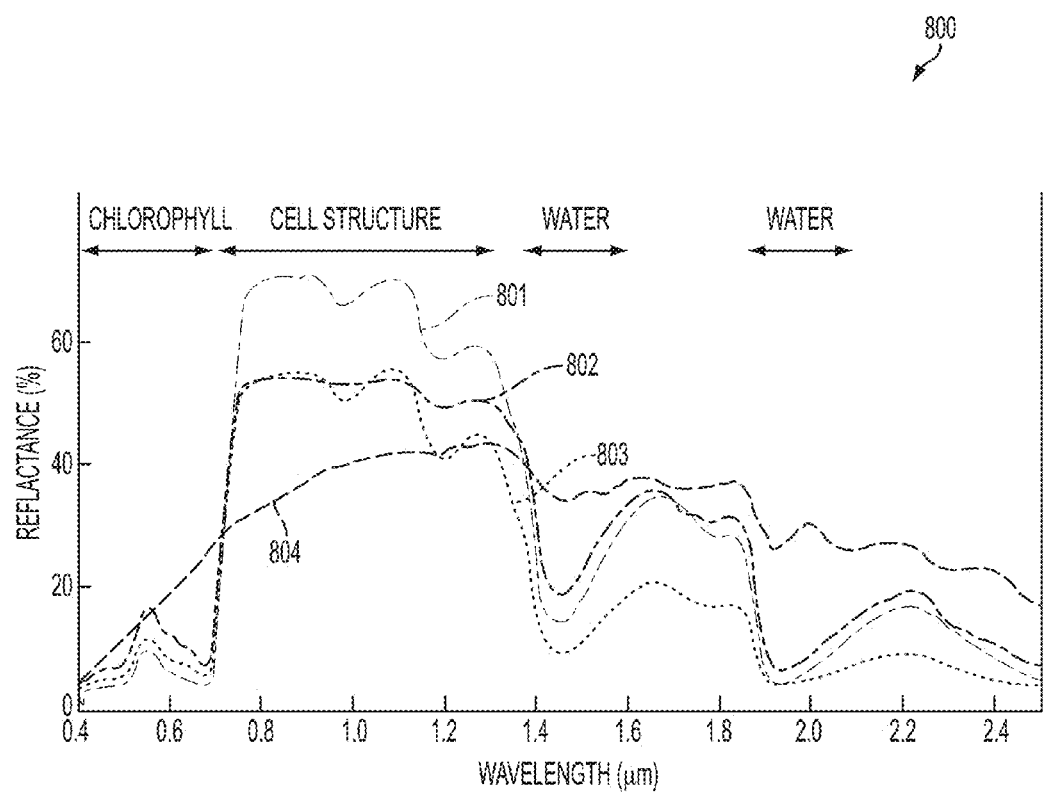
FIG. 8 shows the reflectance spectra of different types of green vegetation compared with dry, yellowed grass.

Remote sensing or hyper-spectral imaging may also be used for agriculture as well as vegetation monitoring. For example, hyper-spectral data may be used to detect the chemical composition of plants, which can be used to detect the nutrient and water status of crops. FIG. 8 illustrates the reflectance spectra 800 of different types of green vegetation compared with dry, yellowed grass. In the visible spectra, the shape may be determined by absorption effects from chlorophyll and other leaf pigments. The reflectance rises rapidly across the boundary between red and infrared wavelengths, which may be due to interactions with the internal cellular structure of leaves. Leaf structure may vary significantly between plant species, as well as from plant stress. Beyond 1.3 microns the reflectance decreases with increasing wavelength, except for two water absorption bands near 1.4 microns and 1.9 microns. Illustrated in FIG. 8 are the reflectance for green grass 801, walnut tree canopy 802, fir tree 803 and senescent 804, which is dry, yellowed grass.

Figure 9:
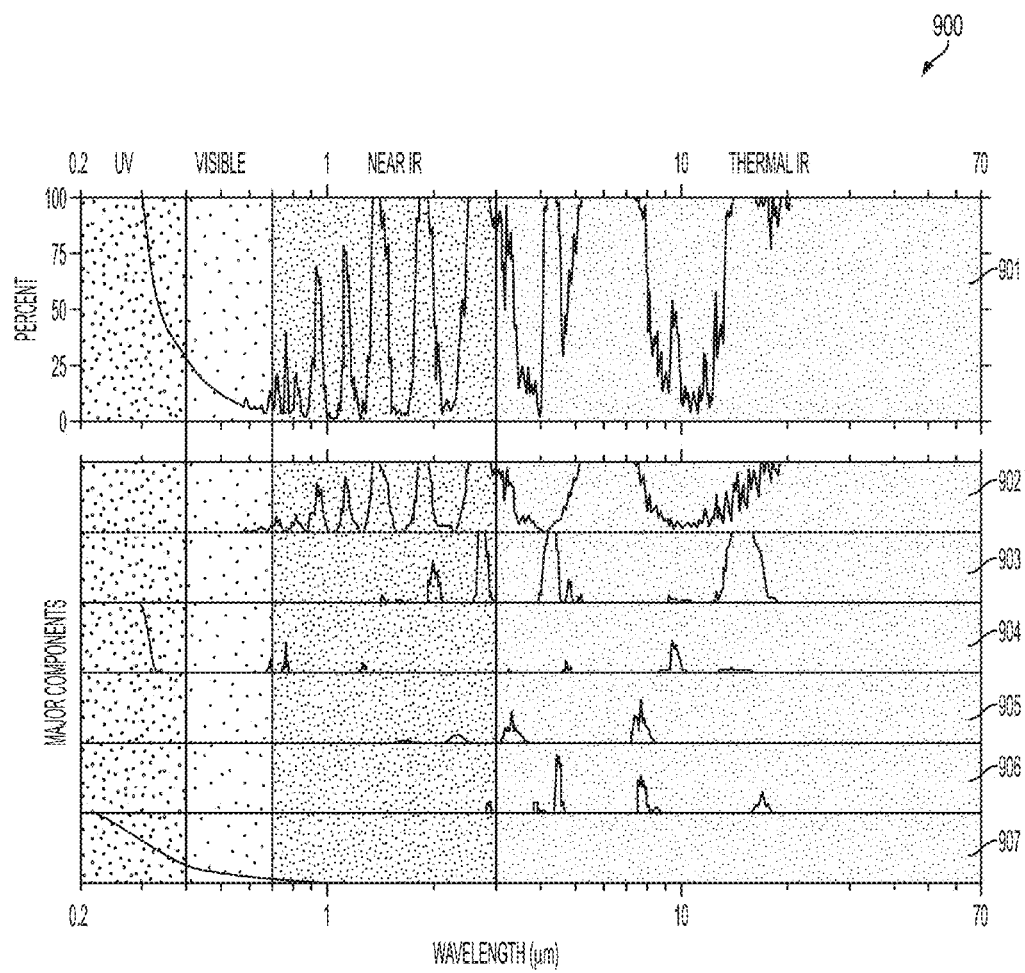
FIG. 9 illustrates the atmospheric absorption and scattering of greenhouse gases at different wavelengths.

Active remote sensing may also be used to measure or monitor gases in the earth's atmosphere, including greenhouse gases, environmental pollutants and aerosols. For instance, greenhouse gases are those that can absorb and emit infrared radiation: In order, the most abundant greenhouse gasses in the Earth's atmosphere are: water vapor ($H_2O$), carbon dioxide ($CO_2$), methane ($CH_4$), nitrous oxide ($N_2O$) and ozone ($O_3$). FIG. 9 shows the atmospheric absorption and scattering of greenhouse gases 900 at different wavelengths. Included in this figure are the total absorption and scattering 901, along with the breakdown by major components: water vapor 902, carbon dioxide 903, oxygen and ozone 904, methane 905, and nitrous oxide 906. Also shown is the Rayleigh scattering 907 through the atmosphere, which dominates at shorter wavelengths, particularly wavelengths shorter than about 1 micron. In one embodiment, environmental concerns of climate change have led to the need to monitor the level of carbon dioxide in the atmosphere, and this may be achieved, for example, by performing spectroscopy in the vicinity of 1.6 microns and 2 microns.

Figure 10:
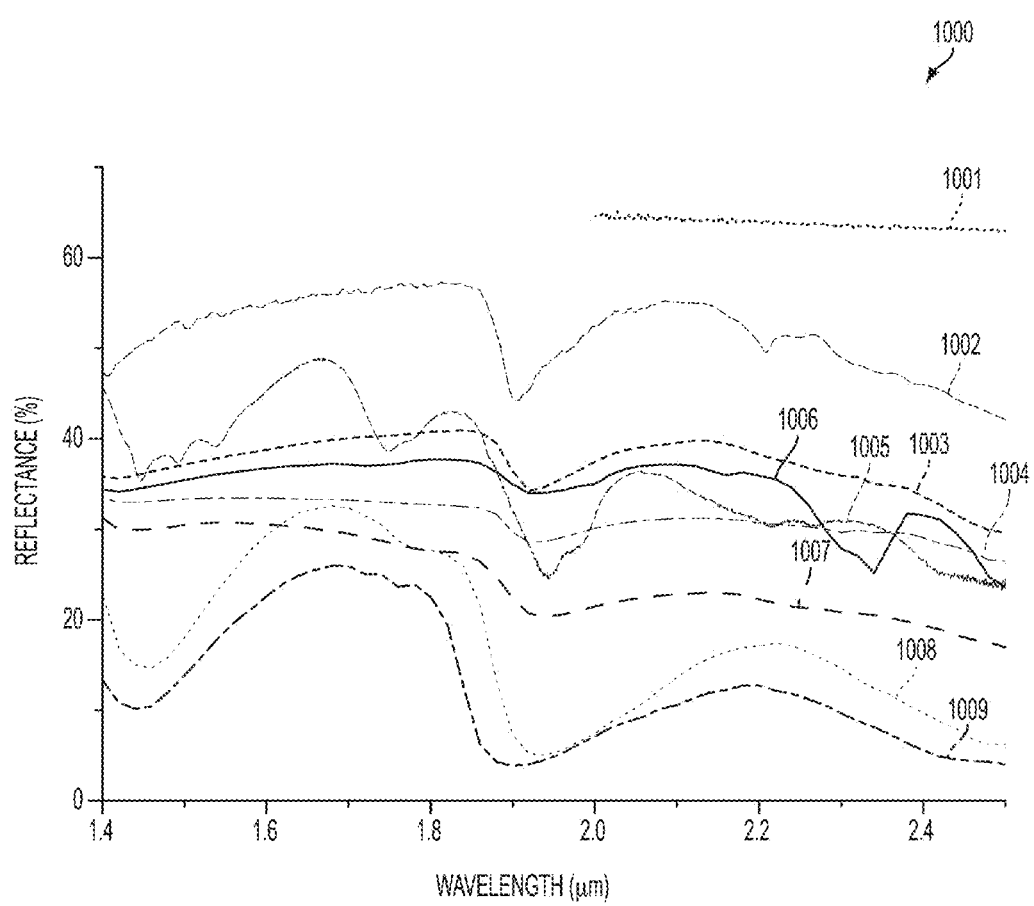
FIG. 10 overlays the reflectance for different building materials from the ASTER spectra library.

In yet another embodiment, different building materials may be identified and distinguished from surrounding vegetation and forestry. FIG. 10 overlays different reflectance data 1000 for samples cataloged in the ASTER spectra library (http://speclib.jpl.nasa.gov). This library has been made available by NASA as part of the Advanced Spaceborne Thermal Emission and Reflection Radiometer, ASTER, imaging instrumentation program. Included in this and other libraries are reflection spectra of natural and man-made materials, including minerals, rocks, soils, water and snow. In FIG. 10 several spectra are included over the SWIR atmospheric transmission bands, and the water absorption between approximately 1.8 and 2 microns has been blocked out (features in there are either due to water or would be masked by the atmospheric moisture). Included in the graph are the spectra for silver metallic paint 1001, light brown loamy sand 1002, construction concrete-1 1003, construction concrete-cement 1004, gypsum 1005, asphaltic concrete 1006, construction concrete-bridges 1007, grass 1008 and conifer trees 1009. As an example, active remote sensing can be used to distinguish different concrete structures, including roadways, buildings, and reinforced structures such as bridges. Also, building materials such as gypsum, painted structures, plywood, and concrete of various sorts, may be distinguished from plant life, soil and trees. Thus, beyond three dimensional imaging, this can add a fourth dimension—namely, identification of objects based on their chemical signature.

Figure 11:
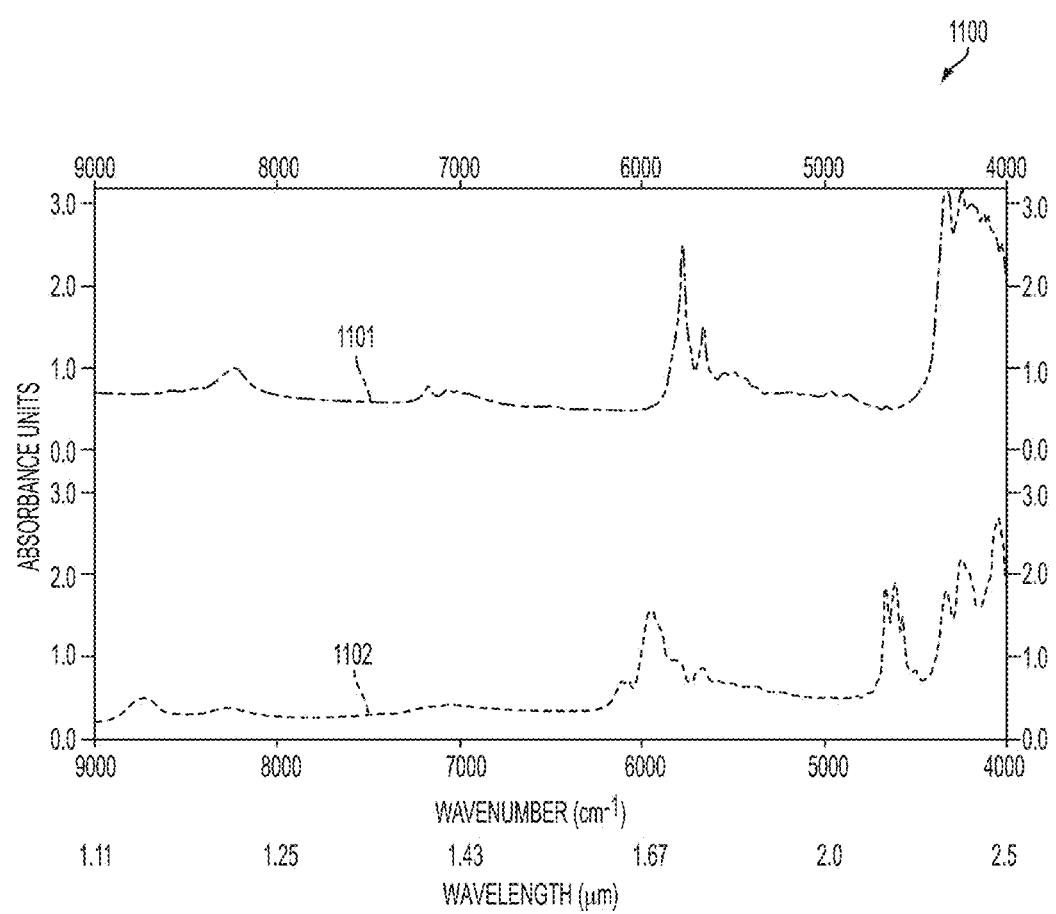
FIG. 11 shows the absorbance for two common plastics, polyethylene and polystyrene.

In a further embodiment, remote sensing or hyper-spectral imaging might be used for process control in a factory or manufacturing setting, particularly when the measurements are to be made at some stand-off or remote distance. As an example, plastics show distinct signatures in the SWIR, and process control may be used for monitoring the manufacture of plastics. Alternately, SWIR light could be used to see through plastics, since the signature for plastics can be subtracted off and there are large wavelength windows where the plastics are transparent. FIG. 11 illustrates the absorbance 1100 for two common plastics: polyethylene 1101 and polystyrene 1102. Because of the hydro-carbon bonds, there are absorption features near 1.7 microns and 2.2-2.5 microns (c.f., discussion on alkanes). In general, the absorption bands in the near infrared are due to overtones and combination bands for various functional group vibrations, including signals from C—H, O—H, C═O, N—H, —COOH, and aromatic C—H groups. It may be difficult to assign an absorption band to a specific functional group due to overlapping of several combinations and overtones. However, with advancements in computational power and chemometrics or multivariate analysis methods, complex systems may be better analyzed. In one embodiment, using software analysis tools the absorption spectrum may be converted to its second derivative equivalent. The spectral differences may permit a fast, accurate, non-destructive and reliable identification of materials. Although particular derivatives are discussed, other mathematical manipulations may be used in the analysis, and these other techniques are also intended to be covered by this disclosure.

Figure 12:
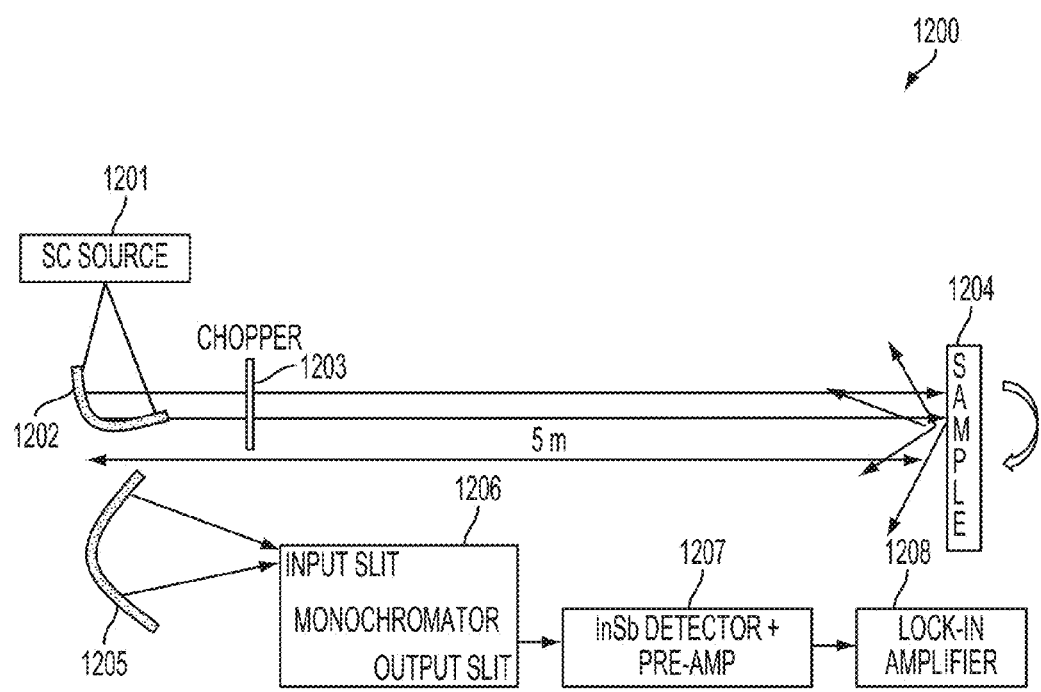
FIG. 12 shows the experimental set-up for a reflection-spectroscopy based stand-off detection system.
Figure 20:
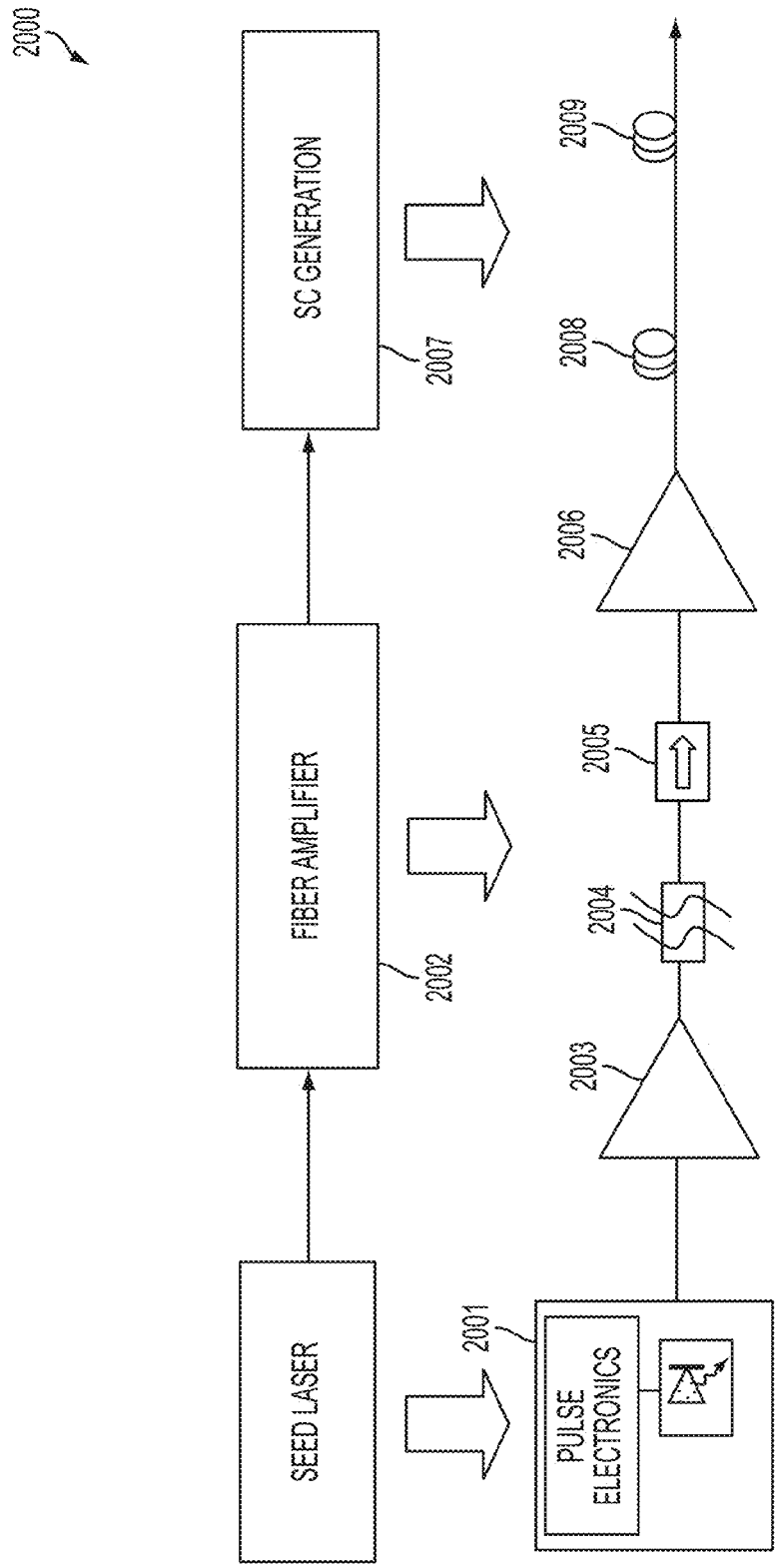
FIG. 20 shows a platform architecture for different wavelength ranges for an all-fiber-integrated, high powered, super-continuum light source.
Figure 21:
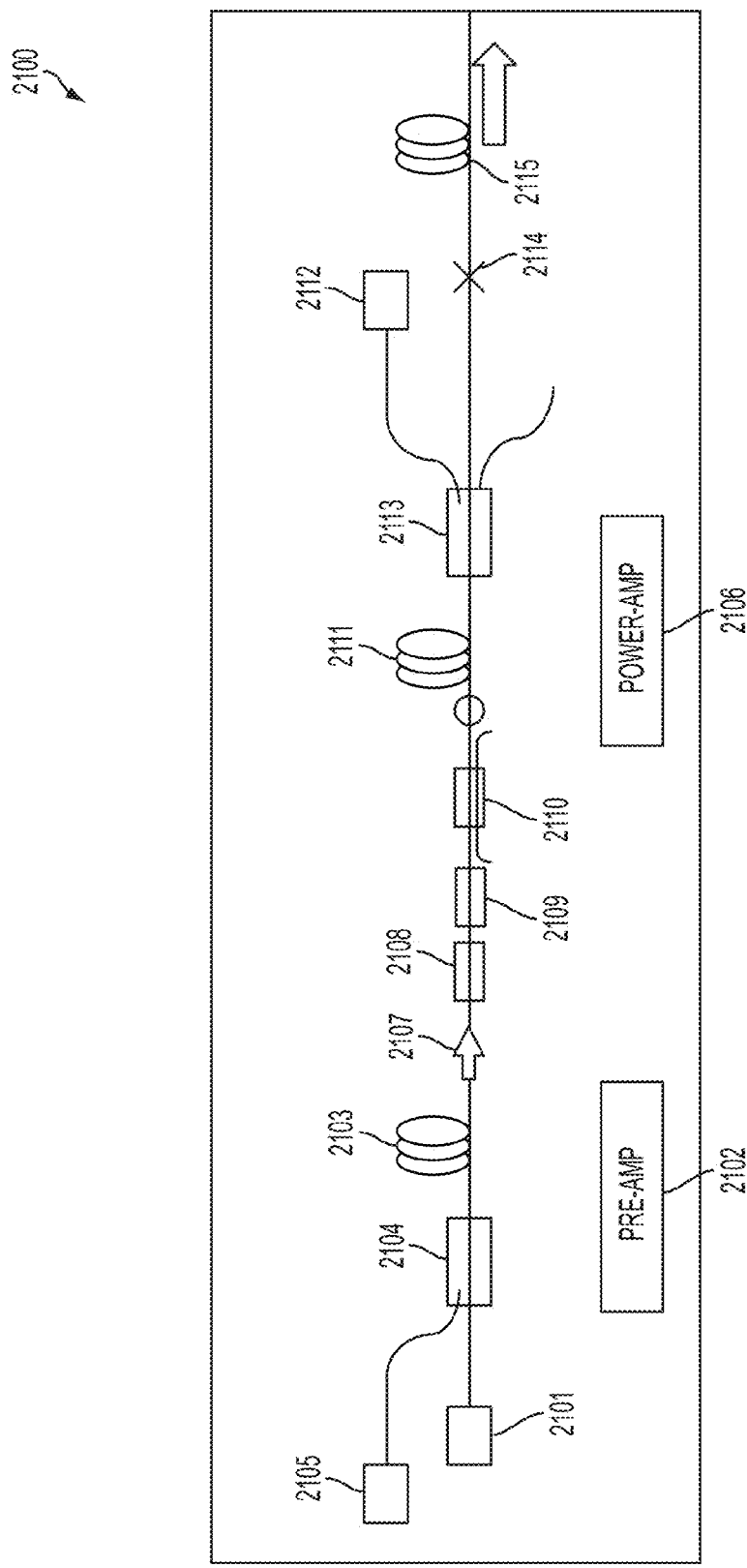
FIG. 21 illustrates one preferred embodiment for a short-wave infrared super-continuum light source.
Figure 23:
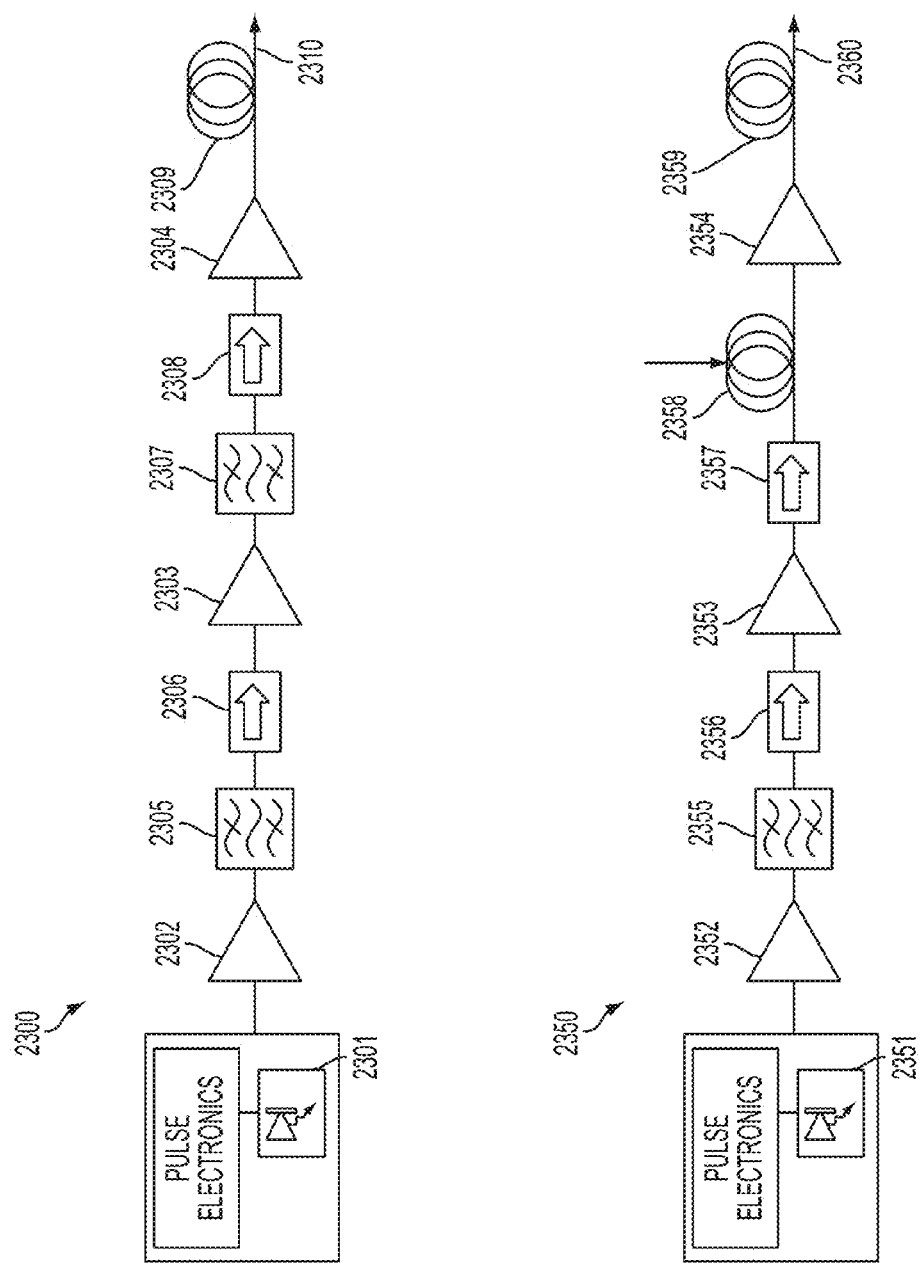
FIG. 23 illustrates high power SWIR-SC lasers that may generate light between approximately 1.4-1.8 microns (top) or approximately 2-2.5 microns (bottom).

In another specific embodiment, experiments have been performed for stand-off detection of solid targets with diffuse reflection spectroscopy using a fiber-based super-continuum source (further described herein). In particular, the diffuse reflection spectrum of solid samples such as explosives (TNT, RDX, PETN), fertilizers (ammonium nitrate, urea), and paints (automotive and military grade) have been measured at stand-off distances of 5 m. Although the measurements were done at 5 m, calculations show that the distance could be anywhere from a few meters to over 150 m. These are specific samples that have been tested, but more generally other materials (particularly comprising hydro-carbons) could also be tested and identified using similar methods. The experimental set-up 1200 for the reflection-spectroscopy-based stand-off detection system is shown in FIG. 12, while details of the SC source 1201 are described later in this disclosure (c.f. FIGS. 20, 21, and 23). First, the diverging SC output is collimated to a 1 cm diameter beam using a 25 mm focal length, 90 degrees off-axis, gold coated, parabolic mirror 1202. To reduce the effects of chromatic aberration, refractive optics are avoided in the setup. All focusing and collimation is done using metallic mirrors that have almost constant reflectivity and focal length over the entire SC output spectrum. The sample 1204 is kept at a distance of 5 m from the collimating mirror 1202, which corresponds to a total round trip path length of 10 m before reaching the collection optics 1205. A 12 cm diameter silver coated concave mirror 1205 with a 75 cm focal length is kept 20 cm to the side of the collimation mirror 1202. The mirror 1205 is used to collect a fraction of the diffusely reflected light from the sample, and focus it into the input slit of a monochromator 1206. Thus, the beam is incident normally on the sample 1204, but detected at a reflection angle of $\tan^{-1}(0.2/5)$ or about 2.3 degrees. Appropriate long wavelength pass filters mounted in a motorized rotating filter wheel are placed in the beam path before the input slit 1206 to avoid contribution from higher wavelength orders from the grating (300 grooves/mm, 2 μm blaze). The output slit width is set to 2 mm corresponding to a spectral resolution of 10.8 nm, and the light is detected by a 2 mm×2 mm liquid nitrogen cooled (77K) indium antimonide (InSb) detector 1207. The detected output is amplified using a trans-impedance pre-amplifier 1207 with a gain of about 105V/A and connected to a lock-in amplifier 1208 setup for high sensitivity detection. The chopper frequency is 400 Hz, and the lock-in time constant is set to 100 ms corresponding to a noise bandwidth of about 1 Hz. These are exemplary elements and parameter values, but other or different optical elements may be used consistent with this disclosure.

Three sets of solid samples are chosen to demonstrate the stand-off diffuse reflection spectra measurement in the laboratory. The first set comprises 'Non-hazardous Explosives for Security Training and Testing' (NESTT) manufactured by the XM Division of VanAken International. These samples contain small amounts of explosives deposited on an inert fused silica powder substrate. The experiments are conduced with the following samples—trinitrotoluene (TNT), research department explosive (RDX), Pentaerythritol tetranitrate (PETN), and potassium nitrate. The TNT, RDX and potassium nitrate NESTT samples have 8% (by weight) explosives, while the PETN sample has 4%.

The second sample set consists of ammonium nitrate, urea, gypsum, and pinewood. Ammonium nitrate and urea are common fertilizers, but are also often used as explosives. These samples are ground to a fine powder in a mortar and pestle, and filled to a depth of about 5 mm in a shallow glass container. We also measure the reflection spectrum of a 10 cm diameter×0.5 cm thick Gypsum ($CaSO_4.2H_2O$) disk and a 5 cm×5 cm×0.5 m piece of pine wood, since these samples are relevant for the remote sensing community (minerals and vegetation).

The final set of samples is selected to distinguish between commercial automotive and military vehicle paints based on their reflection signatures. Red, black, and green acrylic based spray paints are obtained from an auto supply store and sprayed 3 coats on different areas of a sanded Aluminum block to make the automotive paint samples. The sample of the military paint consisted of an Aluminum block coated with a chemical agent resistant coating (CARC) green paint.

Figure 13:
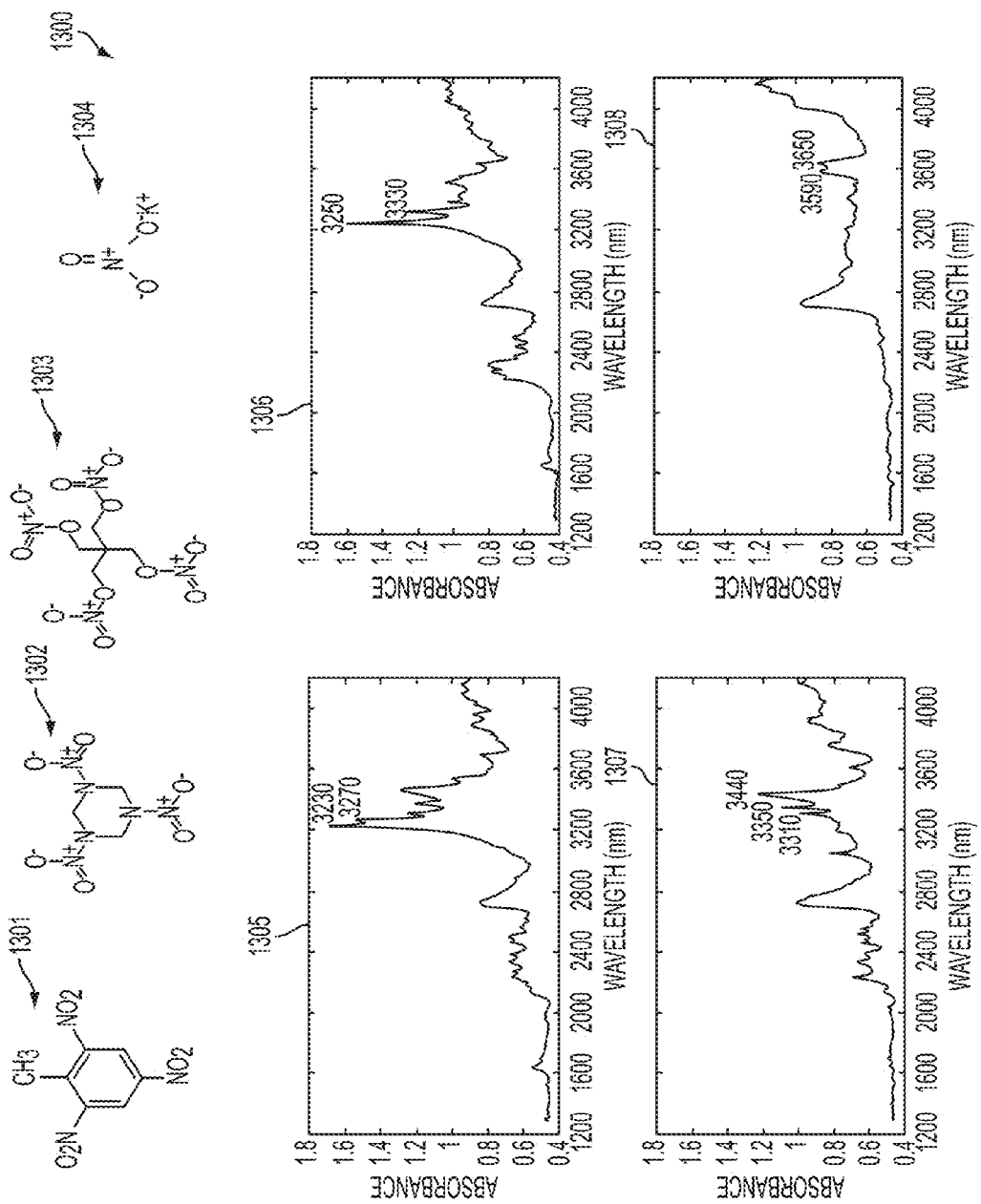
FIG. 13 illustrates the chemical structure and molecular formula for various explosives, along with the absorbance spectra obtained using a super-continuum source.

The chemical structure and molecular formula of the 4 NESTT samples are shown in FIG. 13 (1301, 1302, 1303, 1304), while the absorbance spectra obtained using the SC source are shown below in the same FIG. 1305, 1306, 1307, 1308). For each sample, the positions of the strongest/unique peaks have been labeled for clarity. TNT 1301, 1305 belongs to a class of compounds known as nitro-aromatics, in which the carbon directly attached to the nitro ($NO_2$) group is part of an aromatic ring. The strongest peaks in the spectrum observed at 3230 nm and 3270 nm are due to the fundamental C—H stretching vibrations in the aromatic ring. There are also features between 2200-2600 nm, which may arise from the combination between the C—H stretch and C—H bend vibrations. RDX 1302, 1306 belongs to the nitramines class containing the N—$NO_2$ bond and also has multiple features in the 3200-3500 nm band due to the C—H stretch vibrations. This spectrum also contains the C—H combination bands from 2200-2600 nm. PETN 1303, 1307 is classified as a nitrate ester containing the C—O—$NO_2$ bond, and its reflection spectrum is characterized by a triplet of peaks at 3310 nm, 3350 nm and 3440 nm due to the C—H stretch vibration from the aliphatic groups. The C—H combination band is also present from 2200-2600 nm. Potassium nitrate 1304, 1308 being an inorganic compound does not contain any absorption features due to the C—H bond present in the other three samples. Instead, the unique spectral feature for this sample is a pair of peaks at 3590 nm and 3650 nm, which arise due to the first overtone of the asymmetric N—O stretching vibration of the nitrate ion ($NO_3^-$).

Figure 14A:
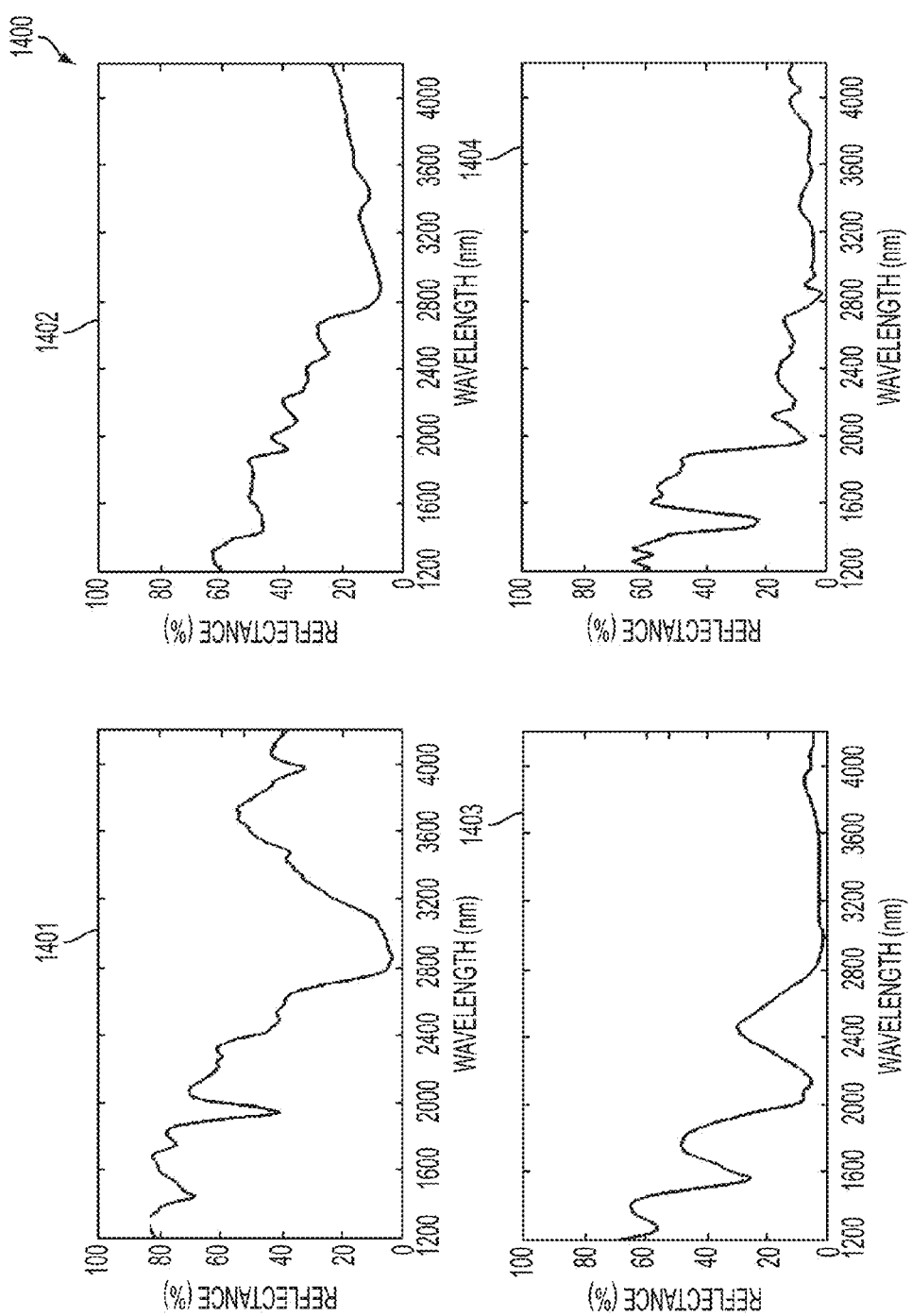
FIG. 14A shows the reflection spectra for gypsum, pine wood, ammonium nitrate and urea.

FIG. 14A illustrates the reflection spectra 1400 for gypsum 1401, pinewood 1402, ammonium nitrate 1403 and urea 1404. The predominant spectral features in the gypsum 1401 ($CaSO_4.2H_2O$) reflectance occur due to the fundamental as well as combination bands of the water molecule near 1450 nm, 1750 nm, 1940 nm and 2860 nm. In addition, small dips in the spectrum at 2220, 2260 and 2480 nm which arise due to the first overtone of the S—O bending vibration. Moreover, the valley at 3970 nm occurs due to the first overtone of the —O—S—O stretching vibration of the sulfate ($SO_4^{2-}$) ion. The pine wood spectrum 1402 comprises of bands due to its main constituents—cellulose, lignin and water. The valleys at 1450 nm, 1920 nm and 2860 nm are attributed to water. The dip at 2100 nm is due to the first overtone of the C—O asymmetric stretch, the one at 2270 nm due to the combination band of O—H and C—H, and the one at 2490 nm due to combination band of C—H and C—O. Finally, the broad feature around 3450 nm is due to the C—H stretching vibration. The ammonium nitrate ($NH_4NO_3$) spectrum 1403 has three prominent features in the near-IR region. The dip at 1270 nm is due to the combination of N—H stretching and N—H bending vibrations, while the dip at 1570 nm is due to the first overtone of N—H stretch. The doublet at 2050 nm and 2140 nm is possibly due to the second overtone of the N—H bending vibrations, while the fundamental N—H stretch appears as a broad feature around 3000 nm. Urea ($NH_2)_2CO$ 1404 has two amide (—$NH_2$) groups joined by a carbonyl (C═O) functional group. The absorption line at 1490 nm occurs due to the third overtone of the C═O stretching vibration while the line at 1990 nm is due to the second overtone of the same.

Figure 14B:
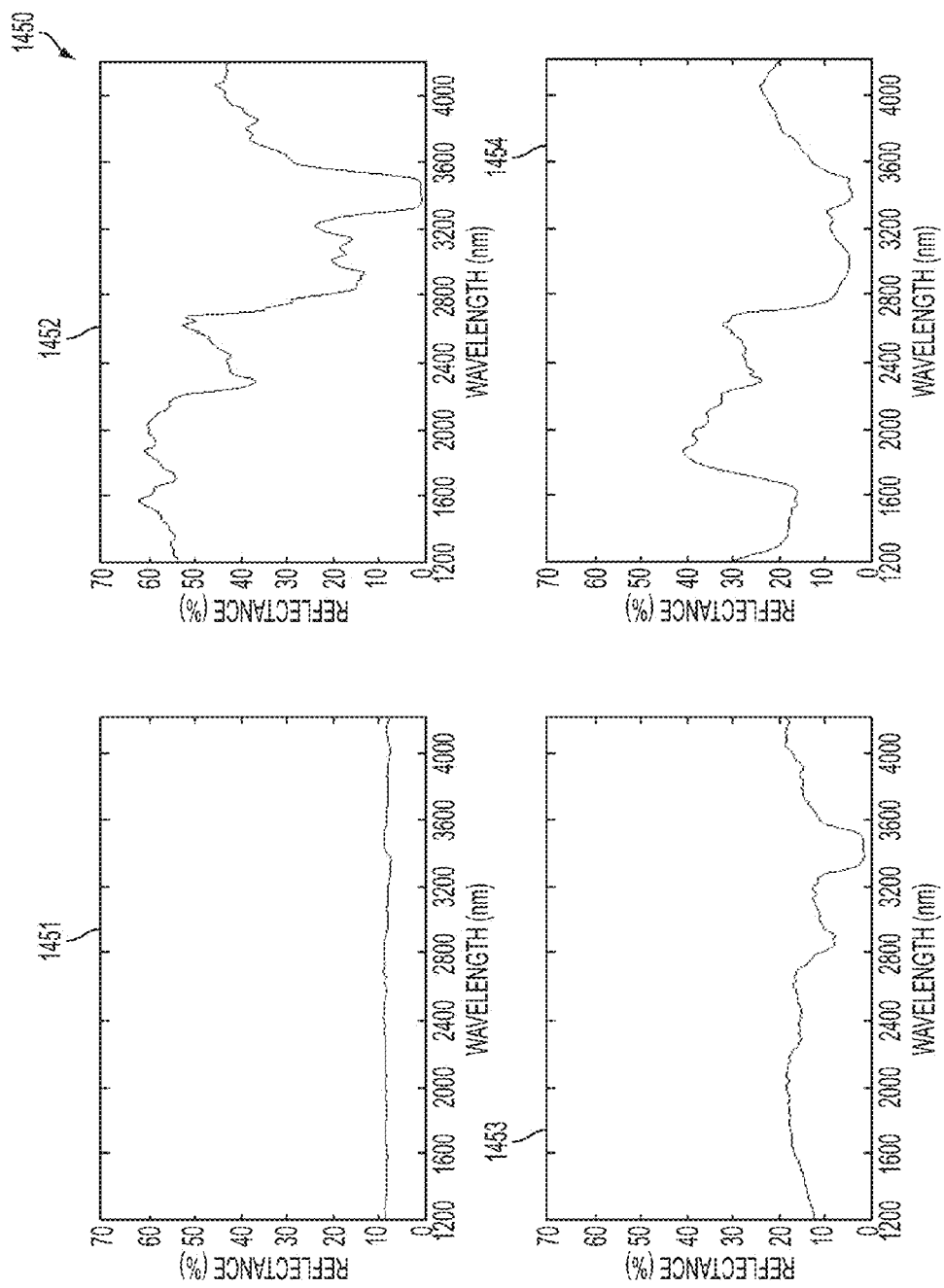
FIG. 14B illustrates the reflection spectra for three commercial automotive paints and military grade CARC paint (chemical agent resistant coating) (reflectance in this case are in arbitrary units).

FIG. 14B shows the reflection spectra 1450 for three commercial automotive paints 1451, 1452, 1453 and military grade CARC (chemical agent resistant coating) paint 1454. The paints consist of a complex mixture of many different chemicals, and, hence, it is very difficult to identify individual absorption lines. Since all four paints contain a variety of organic compounds, features are observed between 3200-3500 nm from the C—H stretch and from 2200-2600 nm due to the C—H stretch and C—H bond combination band. However, the primary difference between the automotive 1451, 1452, 1453 and CARC paint 1454 is the presence of a strong dip between 1200-1850 nm in the latter, which might be attributed to the absorption from Cobalt chromite—a green pigment found in CARC-green.

Figure 15:
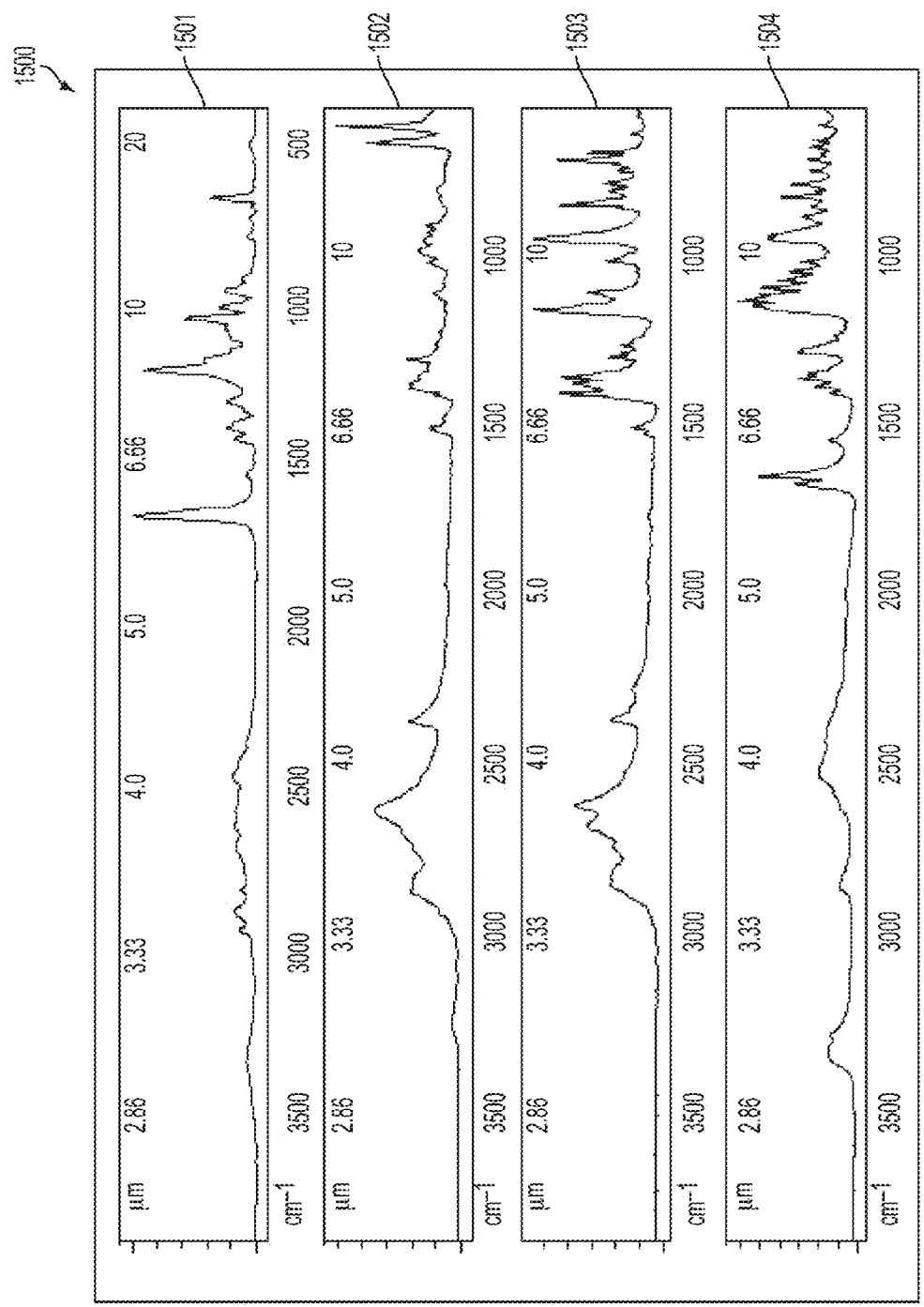
FIG. 15 shows the mid-wave infrared and long-wave infrared absorption spectra for various illicit drugs. It is expected that overtone and combination bands should be evident in the SWIR and near-infrared wavelength bands.

Thus, FIGS. 13 and 14 show that various materials, including explosives, fertilizers, vegetation, and paints have features in the near-infrared and SWIR that can be used to identify the various samples. Although stronger features are found in the mid-infrared, the near-infrared may be easier to measure due to higher quality detection systems, more mature fiber optics and light sources, and transmission through atmospheric transmission windows. Because of these distinct spectral signatures, these materials could also be detected using active remote sensing or hyper-spectral imaging, as described in this disclosure. These are just particular samples that have been tested at stand-off distances, but other materials and samples may also be identified using the SWIR remote sensing or hyper-spectral imaging methods, and these samples are also intended to be covered within this disclosure. As just another example, illicit drugs may be detectable using remote sensing or hyper-spectral imaging. FIG. 15 shows the mid-wave infrared and long-wave infrared absorption spectra 1500 for various illicit drugs. The absorbance for cocaine 1501, methamphetamine 1502, MDMA (ecstasy) 1503, and heroin 1504 are plotted versus wavelength from approximately 2.5-20 microns. Although the fundamental resonances for these drugs may lie in the longer wavelength regions, there are corresponding overtones and combination bands in the SWIR and near-infrared wavelength range. Therefore, the active remote sensing or hyper-spectral imaging techniques described herein may also be applicable to detecting illicit drugs from aircraft, vehicles, or hand held devices.

Detection Systems

As discussed earlier, the active remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 16A:
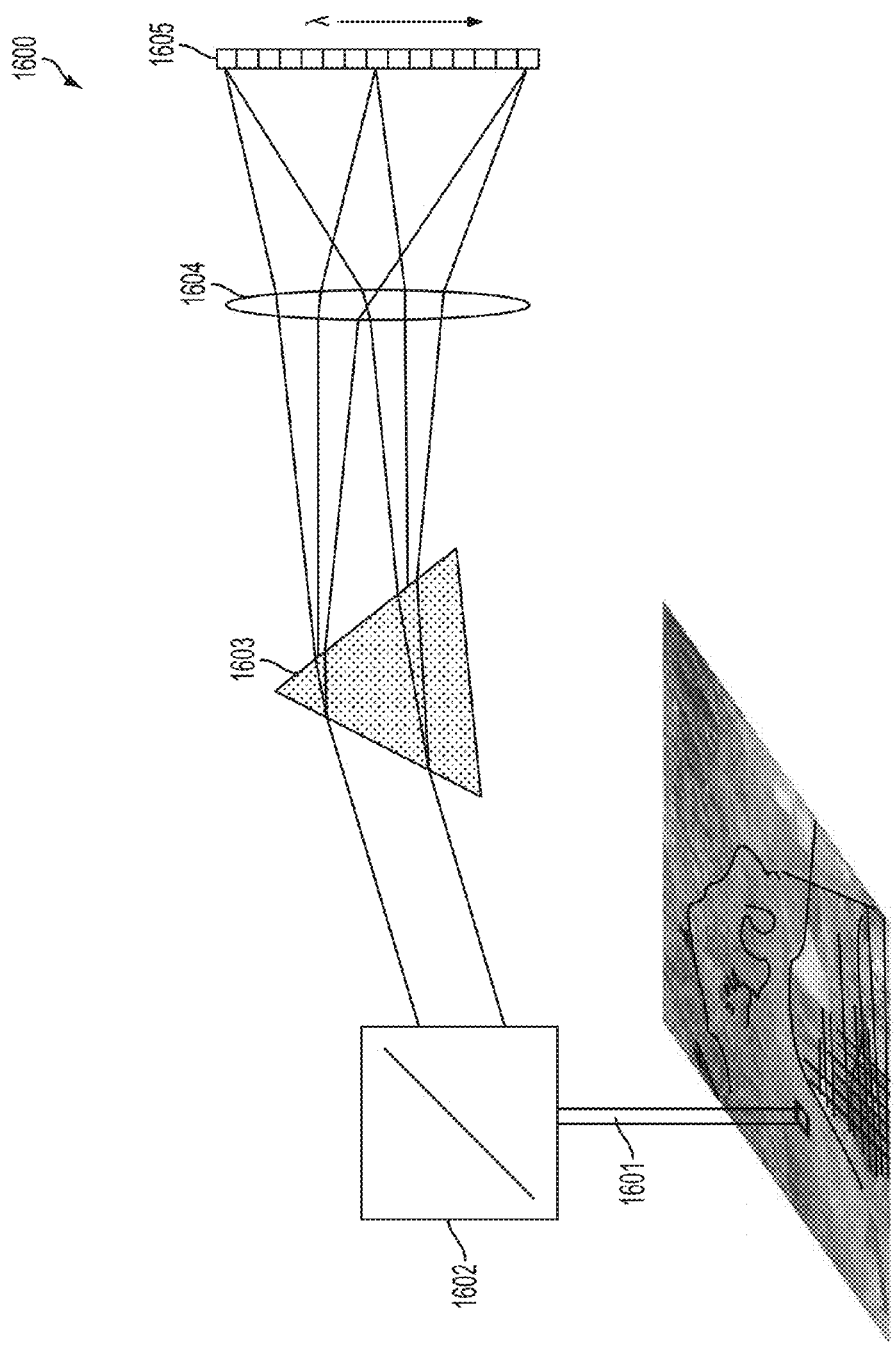
FIG. 16A is a schematic diagram of the basic elements of an imaging spectrometer.

In another embodiment, an imaging spectrometer may be used to detect the light received from the sample. For example, FIG. 16A shows a schematic diagram 1600 of the basic elements of an imaging spectrometer. The input light 1601 from the sample may first be directed by a scanning mirror and/or other optics 1602. An optical dispersing element 1603, such as a grating or prism, in the spectrometer may split the light into many narrow, adjacent wavelength bands, which may then be passed through imaging optics 1604 onto one or more detectors or detector arrays 1605. Some sensors may use multiple detector arrays to measure hundreds of narrow wavelength bands.

Figure 16B:
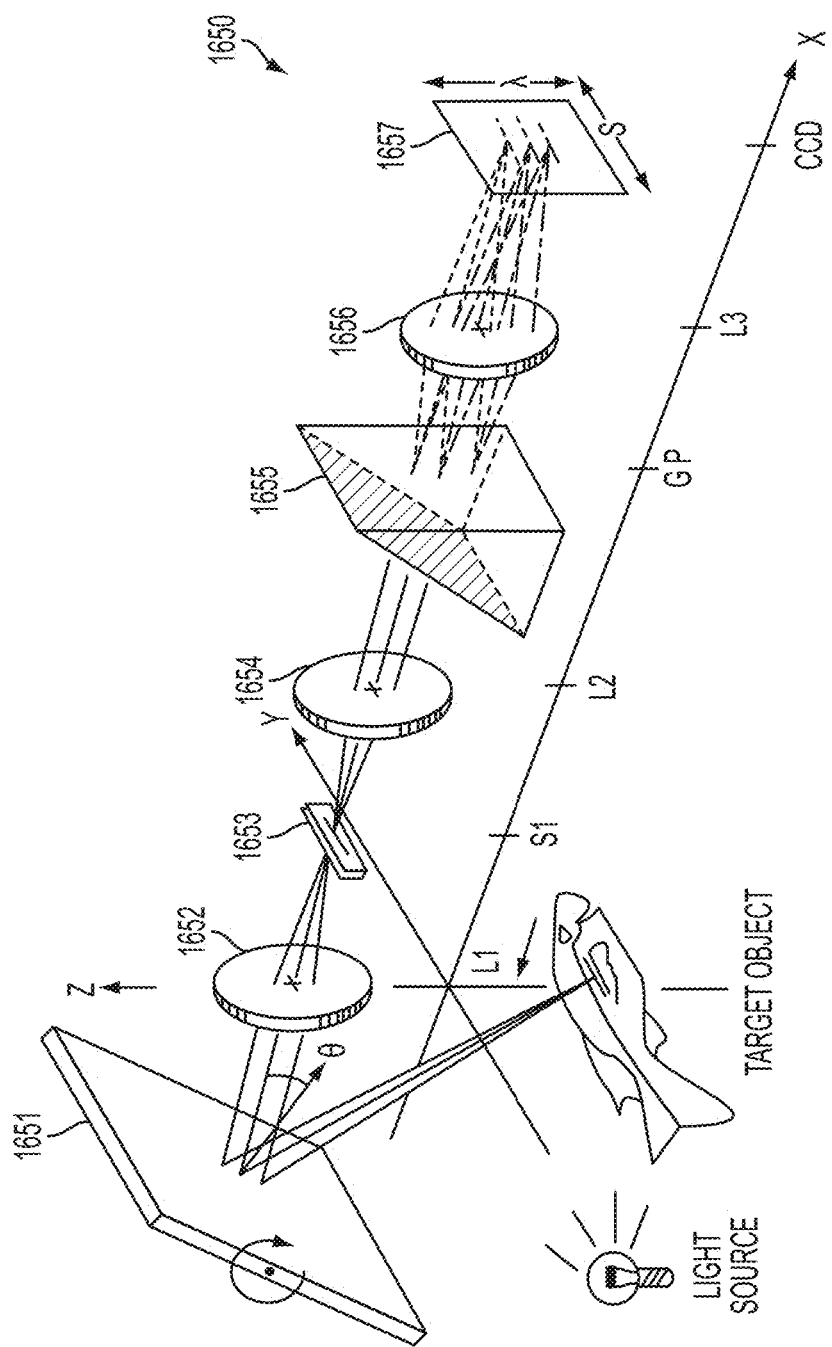
FIG. 16B illustrates one example of a typical imaging spectrometer used in hyper-spectral imaging systems.

An example of a typical imaging spectrometer 1650 used in hyper-spectral imaging systems is illustrated in FIG. 16B. In this particular embodiment, the input light may be directed first by a tunable mirror 1651. A front lens 1652 may be placed before the entrance slit 1653 and the collector lens 1654. In this embodiment, the dispersing element is a holographic grating with a prism 1655, which separates the different wavelength bands. Then, a camera lens 1656 may be used to image the wavelengths onto a detector or camera 1657.

FIGS. 16A and 16B provide particular examples, but some of the elements may not be used, or other elements may be added, and these embodiments are also intended to be covered by this disclosure. For instance, a scanning spectrometer may be used before the detector, where a grating or dispersive element is scanned to vary the wavelength being measured by the detector. In yet another embodiment, filters may be used before one or more detectors to select the wavelengths or wavelength bands to be measured. This may be particularly useful if only a few bands or wavelengths are to be measured. The filters may be dielectric filters, Fabry-Perot filters, absorption or reflection filters, fiber gratings, or any other wavelength selective filter. In an alternate embodiment, a wavelength division multiplexer, WDM, may be used followed by one or more detectors or detector arrays. One example of a planar wavelength division multiplexer may be a waveguide grating router or an arrayed waveguide grating. The WDM may be fiber coupled, and detectors may be placed directly at the output or the detectors may be coupled through fibers to the WDM. Some of these components may also be combined with the configurations in FIGS. 16A and 16B.

Figure 17:
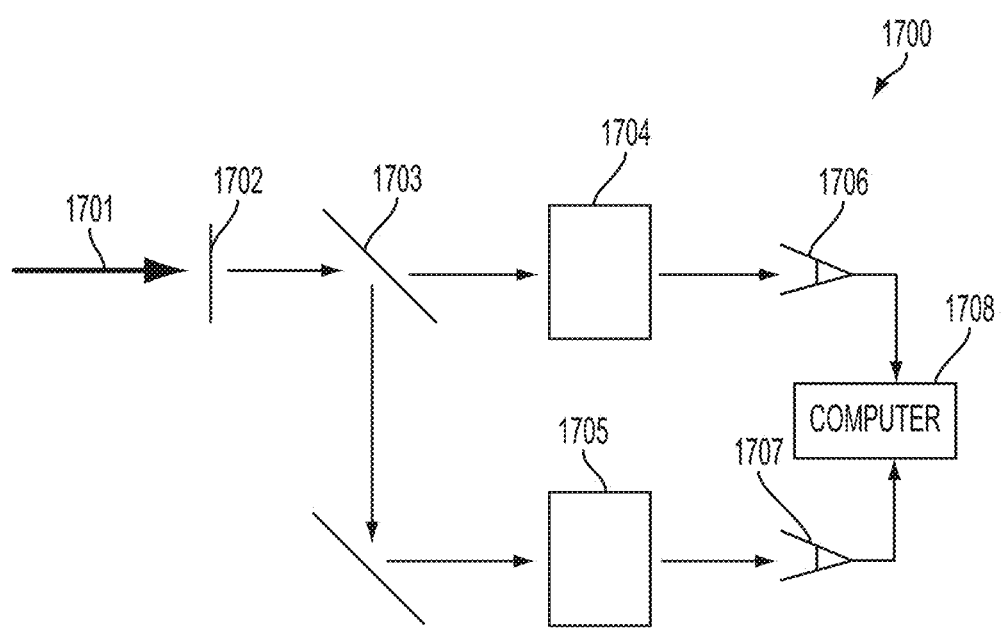
FIG. 17 shows one example of a gas-filter correlation radiometer, which is a detection system that uses a sample of the gas of interest as a spectral filter for the gas.

While the above detection systems could be categorized as single path detection systems, it may be advantageous in some cases to use multi-path detection systems. In one embodiment, when the aim is to measure particular gases or material (rather than identify out of a library of materials), it may advantageous to use gas-filter correlation radiometry (GFCR), such as 1700 in FIG. 17. A GFCR is a detection system that uses a sample of the gas of interest as a spectral filter for the gas. As shown in FIG. 17, the incoming radiation 1701 may first be passed through a narrow band pass filter 1702. The beam may then be split by a beam splitter 1703 along two paths; one path comprising a gas cell filled with the gas of interest 1704 (known as the correlation cell) and the other path comprising no gas 1705. The light from each path may then be measured using two detectors 1706, 1707, and the signals may then be analyzed 1708. The difference in the transmission along the two paths may correspond primarily to the absorption of the gas along the correlation cell path. This GFCR configuration may be advantageous, for example, in the detection of natural gas. Since the goal is to measure methane and ethane, the correlation cells may contain these gases, either in combination or separately. Although a particular configuration for the GFCR has been described, variations of this configuration as well as addition of other components may also be used and are intended to be covered by this disclosure. For example, collection optics and lenses may be used with this configuration, and various modulation techniques may also be used to increase the signal to noise ratio.

Figure 18:
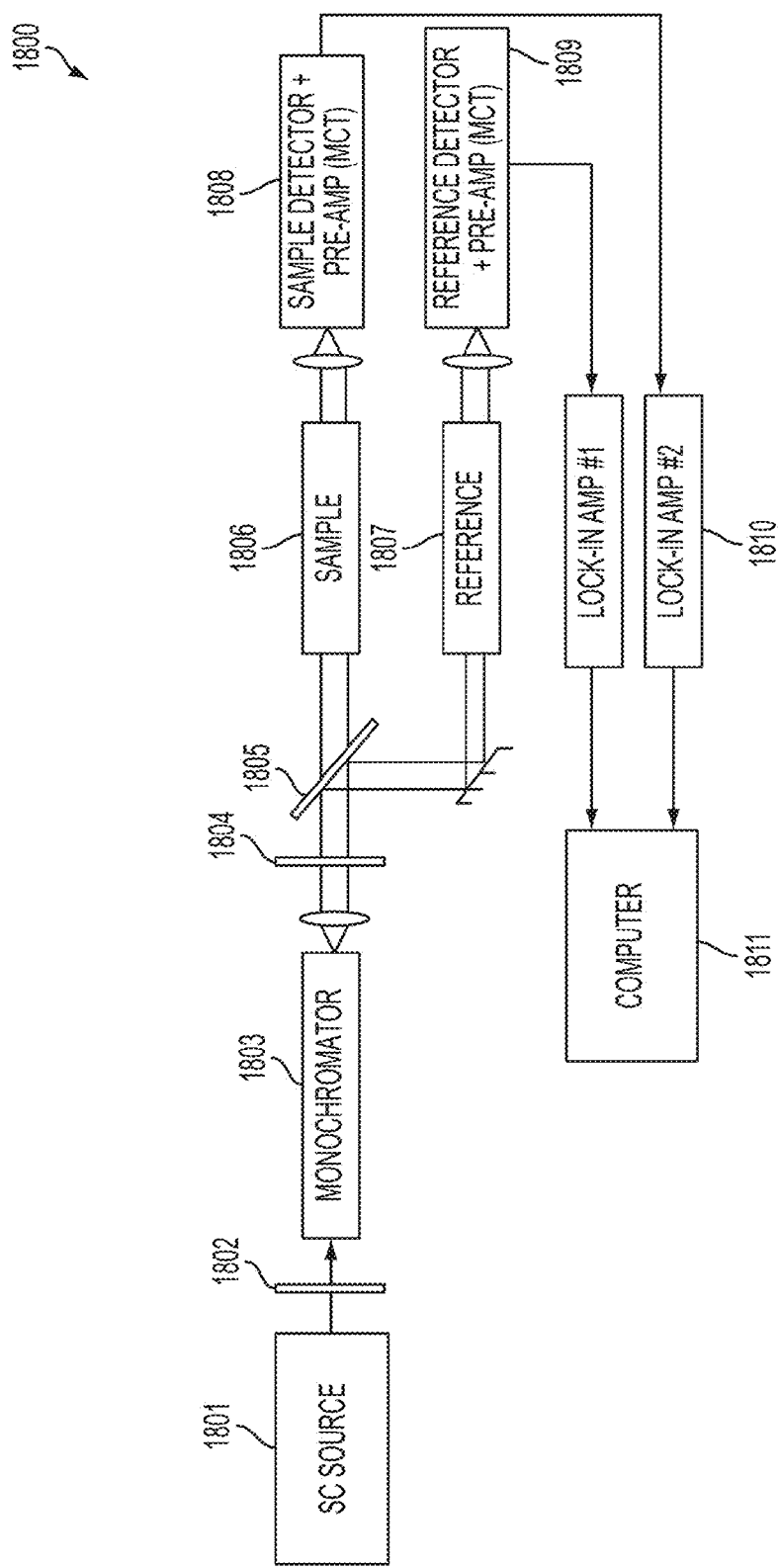
FIG. 18 exemplifies a dual-beam experimental set-up that may be used to subtract out (or at least minimize the adverse effects of) light source fluctuations.

In yet another example of multi-beam detection systems, a dual-beam set-up 1800 such as in FIG. 18 may be used to subtract out (or at least minimize the adverse effects of) light source fluctuations. In one embodiment, the output from an SC source 1801 may be collimated using a calcium fluoride ($CaF_2$)lens 1802 and then focused into the entrance slit of the monochromator 1803. At the exit slit, light at the selected wavelength is collimated again and may be passed through a polarizer 1804 before being incident on a calcium fluoride beam splitter 1805. After passing through the beam splitter 1805, the light is split into a sample 1806 and reference 1807 arm to enable ratiometric detection that may cancel out effects of intensity fluctuations in the SC source 1801. The light in the sample arm 1806 passes through the sample of interest and is then focused onto a HgCdTe detector 1808 connected to a pre-amp. A chopper 1802 and lock-in amplifier 1810 setup enable low noise detection of the sample arm signal. The light in the reference arm 1807 passes through an empty container (cuvette, gas cell etc.) of the same kind as used in the sample arm. A substantially identical detector 1809, pre-amp and lock-in amplifier 1810 is used for detection of the reference arm signal. The signal may then be analyzed using a computer system 1811. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as illustrated in the representative embodiment of FIG. 18 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Light Sources for SWIR and Near Infrared

There are a number of light sources that may be used in the near infrared. To be more specific, the discussion below will consider light sources operating in the short wave infrared (SWIR), which may cover the wavelength range of approximately 1400 nm to 2500 nm. Other wavelength ranges may also be used for the applications described in this disclosure, so the discussion below is merely provided as exemplary types of light sources. The SWIR wavelength range may be valuable for a number of reasons. The SWIR corresponds to a transmission window through water and the atmosphere. Also, the so-called "eye-safe" wavelengths are wavelengths longer than approximately 1400 nm.

Different light sources may be selected for the SWIR based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum sources (SC) may be advantageously used. Also, different fibers may be used for transporting the light, such as fused silica fibers, plastic fibers, mid-infrared fibers (e.g., tellurite, chalcogenides, fluorides, ZBLAN, etc), or a hybrid of these fibers.

Lamps may be used if low power or intensity of light is required in the SWIR, and if an incoherent beam is suitable. In one embodiment, in the SWIR an incandescent lamp that can be used is based on tungsten and halogen, which have an emission wavelength between approximately 500 nm to 2500 nm. For low intensity applications, it may also be possible to use thermal sources, where the SWIR radiation is based on the black body radiation from the hot object. Although the thermal and lamp based sources are broadband and have low intensity fluctuations, it may be difficult to achieve a high signal-to-noise ratio due to the low power levels. Also, the lamp based sources tend to be energy inefficient.

In another embodiment, LED's can be used that have a higher power level in the SWIR wavelength range. LED's also produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in at different wavelength bands, some of which could preferably overlap in spectrum. One advantage of LEDs as well as other solid state components is the compact size that they may be packaged into.

In yet another embodiment, various types of laser diodes may be used in the SWIR wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB) LDs, distributed Bragg reflector (DBR) LDs. Since the LDs have relatively narrow wavelength range (typically under 10 nm), in a preferred embodiment a plurality of LDs may be used that are at different wavelengths in the SWIR. The various LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures such as distributed Bragg reflector LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 nm to 100 nm wide, preferably in the 60 nm to 100 nm range. Although currently SLDs are commercially available in the wavelength range of approximately 400 nm to 1700 nm, SLDs could and may in the future be made that cover a broader region of the SWIR.

Figure 19:
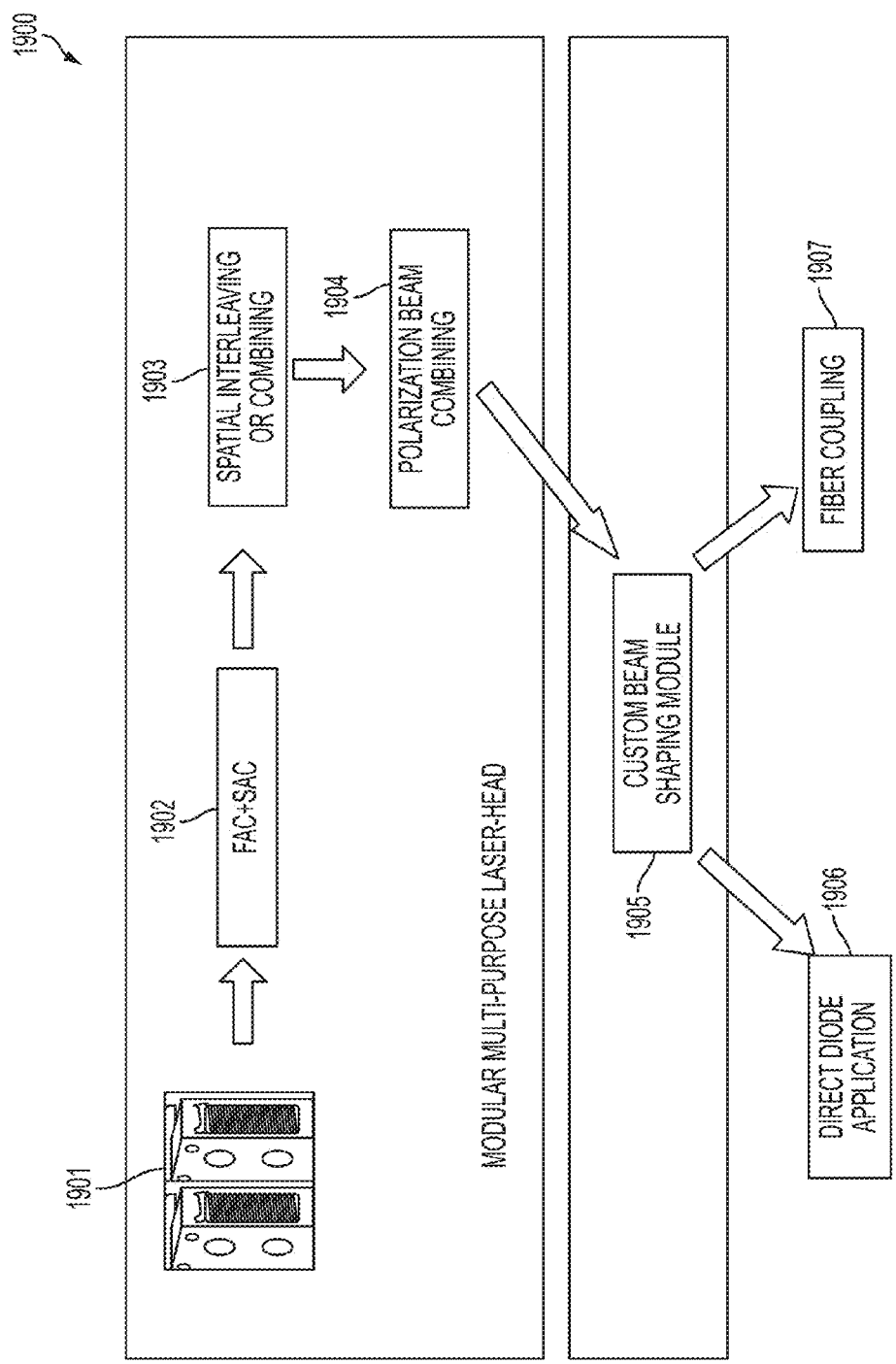
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. FIG. 19 shows an example of the block diagram 1900 or building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

Then, the brightness may be increased by spatially combining the beams from multiple stacks 1903. The combiner may include spatial interleaving, it may include wavelength multiplexing, or it may involve a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In a particular embodiment, the output may then be focused or coupled into a large diameter core fiber. As an example, typical dimensions for the large diameter core fiber range from diameters of approximately 100 microns to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or addition elements may also be used.

SWIR Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until recently, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback laser diode with a wavelength near 1542 nm or 1550 nm, with approximately 0.5-2.0 ns pulsed output, and with a pulse repetition rate between one kilohertz to about 100 MHz or more. The output from the seed laser diode may then be amplified in a multiple-stage fiber amplifier 2002 comprising one or more gain fiber segments. In a particular embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. Exemplary SC fiber lengths may range from a few millimeters to 100 m or more. In one embodiment, the SC generation may occur in a first fiber 2008 where the modulational-instability initiated pulse break-up occurs primarily, followed by a second fiber 2009 where the SC generation and spectral broadening occurs primarily.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime—often called the soliton regime. For high peak powers in the anomalous dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 μm), mid-IR fibers such as fluorides, chalcogenides, or tellurites (for generating SC out to 4.5 μm or longer), photonic crystal fibers (for generating SC between 0.4-1.7 μm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

One example of the SC laser that operates in the SWIR is illustrated in FIG. 21. This SWIR SC source 2100 produces an output of up to approximately 5 W over a spectral range of about 1.5-2.4 microns, and this particular laser is made out of polarization maintaining components. The seed laser 2101 is a distributed feedback laser operating near 1542 nm producing approximately 0.5 nsec pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W laser diode near 940 nm 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses an approximately 4 m length of the 12/130 micron erbium/ytterbium doped fiber 2111 that is counter-propagating pumped using one or more 30 W laser diodes near 940 nm 2112 coupled in through a combiner 2113. An approximately 1-2 m length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
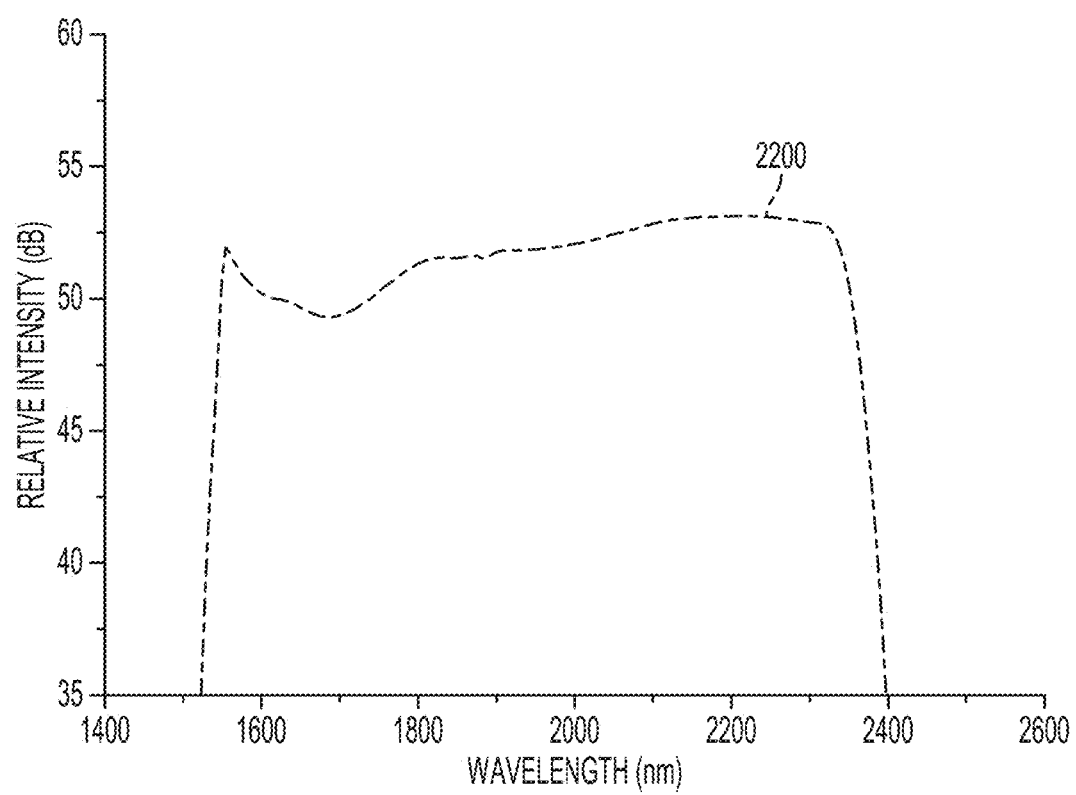
FIG. 22 shows the output spectrum from the SWIR SC laser of FIG. 21 when about 10 m length of fiber for SC generation is used. This fiber is a single-mode, non-dispersion shifted fiber that is optimized for operation near 1550 nm.

If an approximately 10 m length of output fiber is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to about 2500 nm). Also, if extra-dry fibers are used with less O—H content, then the wavelength edge may also reach to a longer wavelength. To generate more spectrum toward the shorter wavelengths, the pump wavelength (in this case around 1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC has been described, different components, different fibers, and different configurations may also be used consistent with this disclosure. For instance, another embodiment of the similar configuration 2100 in FIG. 21 may be used to generate high powered SC between approximately 1060 nm and 1800 nm. For this embodiment, the seed laser 2101 may be a distributed feedback laser diode near 1064 nm, the pre-amplifier gain fiber 2103 may be a ytterbium-doped fiber amplifier with 10/125 microns dimensions, and the pump laser 2105 may be a 10 W laser diode near 915 nm. A mode field adapter may be included in the mid-stage, in addition to the isolator 2107, band pass filter 2108, polarizer 2109 and tap 2110. The gain fiber 2111 in the power amplifier may be a ytterbium-doped fiber with 25/400 microns dimension of about 20 m length. The pump 2112 for the power amplifier may be up to six pump diodes providing 30 W each near 915 nm. For this much pump power, the output power in the SC may be as high as 50 W or more.

In an alternate embodiment, it may be desirous to generate high power SWIR SC over 1.4-1.8 microns and separately 2-2.5 microns (the window between 1.8 and 2 microns may be less important due to the strong water and atmospheric absorption). For example, the top SC source of FIG. 23 can lead to bandwidths ranging from about 1400 nm to 1800 nm or broader, while the lower SC source of FIG. 23 can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber (SMF), high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

In one embodiment, the top of FIG. 23 illustrates a block diagram for an SC source 2300 capable of generating light between approximately 1400 nm and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 nm or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, the bottom of FIG. 23 illustrates a block diagram for an SC source 2350 capable of generating light, for example, between approximately 1900 nm and 2500 nm or broader. As an example, the seed laser diode 2351 can comprise a DFB or DBR laser that generates, for example, several milliwatts of power around 1542 nm or 1553 nm. The fiber pre-amplifier 2352 can comprise an erbium-doped fiber amplifier or an erbium/ytterbium doped double-clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1542 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have a length between approximately 5 m and 50 m, for example. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20, 21, and 23 are that they use all-fiber components, so that the SC laser can be all-fiber, monolithically integrated with no moving parts. The all-integrated configuration can consequently be robust and reliable.

FIGS. 20, 21 and 23 are examples of SC light sources that may be advantageously used for SWIR light generation in various active remote sensing and hyper-spectral imaging applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers. Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In an alternate embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate SWIR light that are intended to be covered by this disclosure.

Figure 24:
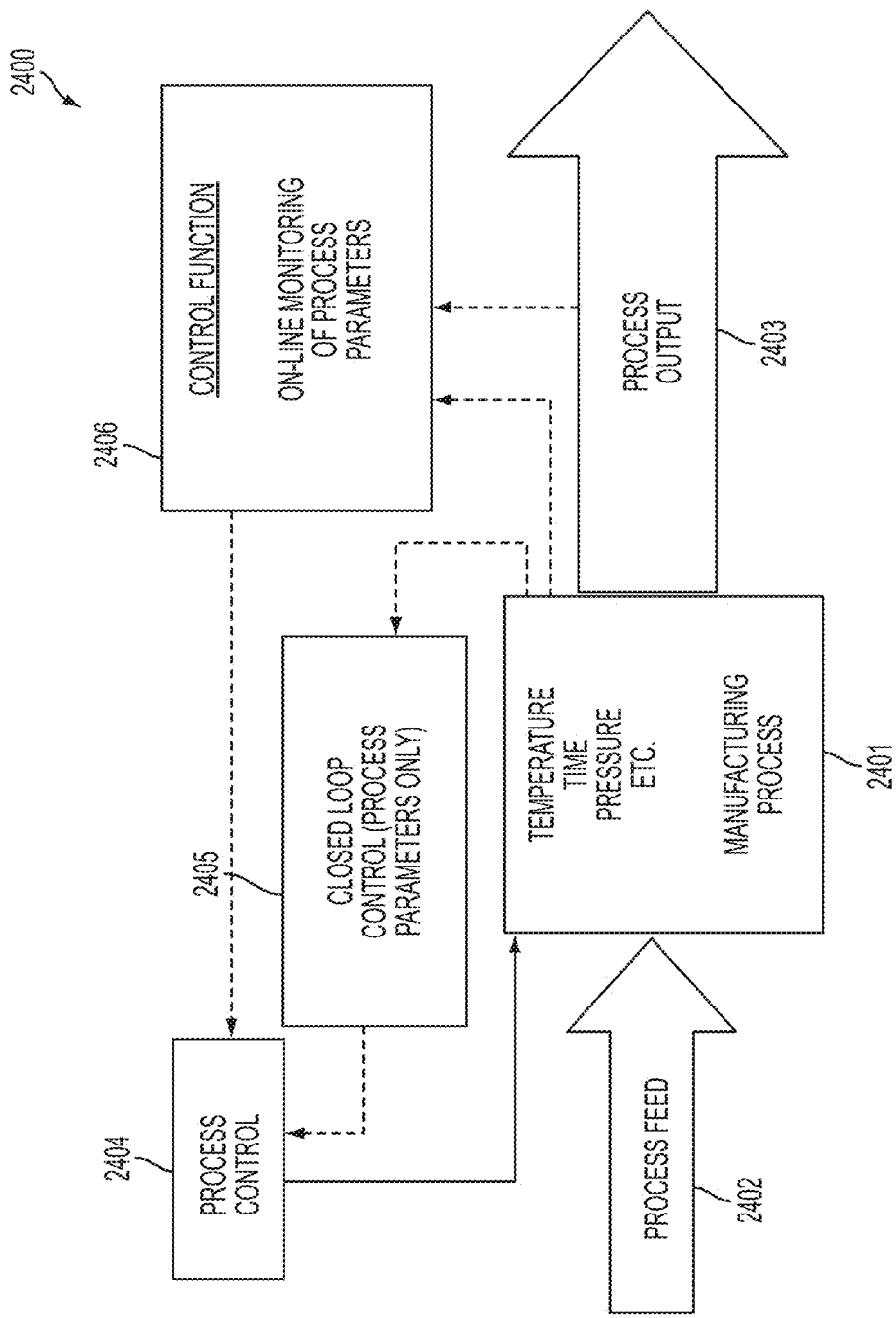
FIG. 24 illustrates a flowchart of a smart manufacturing process.

FIG. 24 illustrates a flowchart 2400 of a smart manufacturing process. The manufacturing process 2401 may have as input the process feed 2402 and result in a process output 2403. A process controller 2404 may at least partially control the manufacturing process 2401, and the controller 2404 may receive inputs from the closed loop control (process parameters) 2405 as well as the on-line monitoring of process parameters 2406. The feedback loops in the process could refine the manufacturing process 2401 and improve the quality of the process output 2403. These are particular embodiments of the use of near-infrared or SWIR spectroscopy in the PAT of the pharmaceutical industry, but other variations, combinations, and methods may also be used and are intended to be covered by this disclosure, such as use in manufacture of plastics or food industry goods.

The discussion thus far has centered on use of near-infrared or SWIR spectroscopy in applications such as identification of counterfeit drugs, detection of illicit drugs, and pharmaceutical process control. Although drugs and pharmaceuticals are one example, many other fields and applications may also benefit from the use of near infrared or SWIR spectroscopy, and these may also be implemented without departing from the scope of this disclosure. As just another example, near-infrared or SWIR spectroscopy may also be used as an analytic tool for food quality and safety control. Applications in food safety and quality assessment include contaminant detection, defect identification, constituent analysis, and quality evaluation. The techniques described in this disclosure are particularly valuable when non-destructive testing is desired at stand-off or remote distances.

In yet another embodiment, near-infrared or SWIR spectroscopy may be used for the assessment of fruit and vegetable quality. Most commercial quality classification systems for fruit and vegetables are based on external features of the product, such as shape, color, size, weight and blemishes. However, the external appearance of most fruit is generally not an accurate guide to the internal eating quality of the fruit. As an example, for avocado fruit the external color is not a maturity characteristic, and its smell is too weak and appears later in its maturity stage. Analysis of the near-infrared or SWIR absorption spectra may provide qualitative and quantitative determination of many constituents and properties of horticulture produce, including oil, water, protein, pH, acidity, firmness, and soluble solids content or total soluble solids of fresh fruits. For example, near-infrared absorbance spectra may be obtained in diffusion reflectance mode for a series of whole 'Hass' avocado fruit. Four oil absorption bands are near 2200-2400 nm ($CH_2$ stretch bend and combinations), with weaker absorption around 750 nm, 1200 nm, and 900-930 nm ranges. On the other hand, near 1300-1750 nm range may be useful for determining the protein and oil content. The 900-920 nm absorbance band may be useful for sugar determination. Although described in the context of grains, fruits, and vegetables, the near-infrared or SWIR spectroscopy may also be valuable for other food quality control and assessment, such as measuring the properties of meats. These and other applications also fall within the scope of this disclosure.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Although the present disclosure has been described in several embodiments, a myriad of changes, variations, alterations, transformations, and modifications may be suggested to one skilled in the art, and it is intended that the present disclosure encompass such changes, variations, alterations, transformations, and modifications as falling within the spirit and scope of the appended claims.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

What is claimed is:

1. A measurement system comprising:
a light source configured to generate an output optical beam, comprising:
    a plurality of semiconductor sources configured to generate an input optical beam;
    a multiplexer configured to receive at least a portion of the input optical beam and to form an intermediate optical beam;
    one or more fibers configured to receive at least a portion of the intermediate optical beam and to form the output optical beam;
    wherein at least a portion of the one or more fibers comprises a fused silica fiber having a core diameter less than 400 microns;
    wherein the output optical beam comprises one or more optical wavelengths, at least a portion of which are between 700 nanometers and 2500 nanometers; and
    wherein the output optical beam has a bandwidth of at least 10 nanometers;
a measurement apparatus configured to receive a received portion of the output optical beam and to deliver a delivered portion of the output optical beam to a sample, wherein the delivered portion of the output optical beam is configured to generate a spectroscopy output beam from the sample; and
a receiver configured to receive at least a portion of the spectroscopy output beam having a bandwidth of at least 10 nanometers and to process the at least a portion of the spectroscopy output beam to generate an output signal;
wherein the light source and the receiver are remote from the sample, wherein the sample comprises plastics or food industry goods, and wherein the measurement system performs non-destructive quality control or constitutive analysis.

2. The system of claim 1, wherein the measurement apparatus is a stand-off detection apparatus, and the spectroscopy output beam is based at least in part on diffuse reflection from the sample.

3. The system of claim 1, wherein the measurement system is used for on-line process control.

4. The system of claim 1, wherein the output signal at least in part determines the sugar content in solid food industry goods.

5. The system of claim 1, wherein the output signal is based on a chemical composition of the sample.

6. A measurement system comprising:
a light source configured to generate an output optical beam, comprising:
    a plurality of semiconductor sources configured to generate an input optical beam;
    a multiplexer configured to receive at least a portion of the input optical beam and to form an intermediate optical beam;
    one or more fibers configured to receive at least a portion of the intermediate optical beam and to form the output optical beam;
    wherein at least a portion of the one or more fibers comprises a fused silica fiber having a core diameter less than 400 microns;
    wherein the output optical beam comprises one or more optical wavelengths, at least a portion of which are between 700 nanometers and 2500 nanometers; and
    wherein the output optical beam has a bandwidth of at least 10 nanometers;
a measurement apparatus configured to receive a received portion of the output optical beam and to deliver a delivered portion of the output optical beam to a sample, wherein the delivered portion of the output optical beam is configured to generate a spectroscopy output beam from the sample; and
a receiver configured to receive at least a portion of the spectroscopy output beam having a bandwidth of at least 10 nanometers and to process the at least a portion of the spectroscopy output beam to generate an output signal;
wherein the output signal is based on a chemical composition of the sample;
wherein the spectroscopy output beam comprises spectral features of hydrocarbons or organic compounds; and
wherein the light source and the receiver are remote from the sample, and wherein the sample comprises plastics or food industry goods.

7. The system of claim 6, wherein the light source comprises a super-continuum laser.

8. The system of claim 6, wherein the measurement apparatus is a stand-off detection apparatus, and the spectroscopy output beam is based at least in part on diffuse reflection from the sample.

9. The system of claim 6, wherein the measurement system is used for non-destructive testing of the sample.

10. The system of claim 6, wherein the measurement system is used for quality control or constitutive analysis of the sample.

11. The system of claim 6, wherein the receiver comprises a wavelength tunable detection system.

12. The system of claim 6, wherein the measurement system is used for on-line process control.

13. The system of claim 1, wherein the output signal corresponds to overtone or combinational bands of the chemical composition of the sample.

14. The system of claim 6, wherein the output signal at least in part determines the sugar content in solid food industry goods.

15. A method of measuring, comprising:
generating an output optical beam, comprising:
    generating an input optical beam from a plurality of semiconductor sources;
    multiplexing at least a portion of the input optical beam and forming an intermediate optical beam; and
    guiding at least a portion of the intermediate optical beam using one or more fibers including a fused silica fiber having a core diameter less than 400 microns; and
    broadening a spectrum of at least a portion of the intermediate optical beam to at least 10 nanometers to form the output optical beam with an output beam broadened spectrum, wherein the output optical beam comprises one or more optical wavelengths between 700 nanometers and 2500 nanometers;

receiving a received portion of the output optical beam and delivering a delivered portion of the output optical beam to a sample comprising plastics or food industry goods located remotely from the generated output optical beam;

generating a spectroscopy output beam having a bandwidth of at least 10 nanometers from the sample, wherein the spectroscopy output beam comprises spectral features based on a chemical composition of the sample;

receiving at least a portion of the spectroscopy output beam; and processing the at least a portion of the spectroscopy output beam and generating an output signal;

wherein the measuring method is used for non-destructive quality control or constitutive analysis.

16. The method of claim 15, wherein the output signal at least in part determines the sugar content in solid food industry goods.

17. The method of claim 15, wherein the measuring method is used for on-line process control.

* * * * *

UNITED STATES PATENT AND TRADEMARK OFFICE
CERTIFICATE OF CORRECTION

PATENT NO.         : 9,897,584 B2
APPLICATION NO.    : 15/711907
DATED              : February 20, 2018
INVENTOR(S)        : Mohammed N. Islam et al.

It is certified that error appears in the above-identified patent and that said Letters Patent is hereby corrected as shown below:

In the Claims

Column 30, Line 49, Claim 13:
After "of claim"
Delete "1"
Insert --6--

Signed and Sealed this
Eighth Day of May, 2018

Andrei Iancu
*Director of the United States Patent and Trademark Office*